US007572822B2

(12) United States Patent
Chakravarty et al.

(10) Patent No.: US 7,572,822 B2
(45) Date of Patent: *Aug. 11, 2009

(54) BIARYL SUBSTITUTED TRIAZOLES AS SODIUM CHANNEL BLOCKERS

(75) Inventors: Prasun K. Chakravarty, Edison, NJ (US); Michael H. Fisher, Flemington, NJ (US); Louis L. Zuegner, III, legal representative, Flemington, NJ (US); William H. Parsons, Belle Mead, NJ (US); Brenda Palucki, Hillsborough, NJ (US); Bishan Zhou, Edison, NJ (US); Min K. Park, Whippany, NJ (US)

(73) Assignee: Merck & Co. Inc., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/011,967

(22) Filed: Jan. 30, 2008

(65) Prior Publication Data
US 2008/0171777 A1  Jul. 17, 2008

Related U.S. Application Data

(63) Continuation of application No. 10/799,230, filed on Mar. 12, 2004, now Pat. No. 7,326,726.

(60) Provisional application No. 60/455,952, filed on Mar. 18, 2003.

(51) Int. Cl.
*A61K 31/4196* (2006.01)
*A61K 31/41* (2006.01)
*C07D 249/08* (2006.01)

(52) U.S. Cl. .................. 514/383; 548/262.2; 548/266.8

(58) Field of Classification Search .................. None
See application file for complete search history.

(56) References Cited

U.S. PATENT DOCUMENTS

| 6,849,636 | B2 | 2/2005 | Waddell et al. | |
|---|---|---|---|---|
| 6,875,782 | B2 | 4/2005 | Cheng et al. | |
| 6,962,936 | B2 | 11/2005 | Hale et al. | |
| RE38,962 | E | 1/2006 | Rossi | |
| 7,019,144 | B2 | 3/2006 | Cho et al. | |
| 7,326,726 | B2* | 2/2008 | Chakravarty et al. | 514/359 |
| 7,459,475 | B2* | 12/2008 | Park et al. | 514/383 |

FOREIGN PATENT DOCUMENTS

| EP | 0572 142 | 5/1993 |
|---|---|---|
| WO | WO 94/22852 | 10/1994 |
| WO | WO 99/32462 | 7/1999 |
| WO | WO 00/57877 | 10/2000 |
| WO | WO 01/68612 | 9/2001 |

OTHER PUBLICATIONS

Patani, et al. Bioisosterism: A Rational Approach in Drug Design, Chem. Rev. 1996, 96, pp. 3147-3176, especially p. 3149.*
Omodei-Sale et al. J. Med. Chem. 26 (8), 1983.*
J. J. Clare et al., "Voltage-Gated Sodium Channels as Therapeutic Targets", 2000, vol. 5, pp. 506-520, Therapeutic Forces.
W. A. Catterall, "Structure and Function of Voltage-Gated Sodium and Calcium Channels", 1991, vol. 1, pp. 5-13, Current Opinion in Neurobiology.
M. D. Baker et al., "Involvement of Na+ Channels in Pain Pathways", 2001, vol. 22, No. 1, pp. 27-31, Trends in Pharmacological Sciences.
J. Mao et al., "Systemic Lidocaine for Neuropathic Pain Relief", 2000, vol. 87, pp. 7-17, Pain.
D. L. Tanellian et al., "Neuropathic Pain Can be Relieved by Drugs That Are Use-dependent Sodium Channel Blockers: Lidocaine, Carbamazepine, and Mexiletine", vol. 74, pp. 949-951, Anesthesiology.
T. Anger et al., "Medicinal Chemistry of Neuronal Voltage-Gated Sodium Channel Blockers", 2001, vol. 44, No. 2, pp. 115-137, J. Med. Chem.
A. Devers et al., "Topical Lidocaine Patch Relieves a Variety of Neuropathic Pain Conditions: An Open-Label Study", 2000, vol. 16, pp. 205-208, The Clinical Journal of Pain.
J. March et al., "Reactions, Mechanisms, and Structure", 2001, pp. 506-512, March's Advanced Organic Chemistry, Fifth Edition.
A. Suzuki et al., "Palladium-Catalyzed Cross-Coupling Reactions of Organoboron Compounds", 1995, vol. 7, pp. 2457-2483, Chemical Reviews.
J. J. Li et al., "1,2-Diarylcyclopentenes as Selective Cyclooxygenase-2 Inhibitors and Orally Active Anti-Infammatory Agents", 1995, vol. 38, pp. 4570-4578, J. of Medicinal Chemistry.
S. R. Piettre et al., "Monoaryl-and Bisaryldihydroxytropolones as Potent Inhibitors of Inositol Monophosphatase", 1997, vol. 40, pp. 4208-4221, J. of Medicinal Chemistry.
A. Giroux et al., "One Pot Biaryl Synthesis Via in Situ Boronate Formation", 1997, vol. 38, No. 22 pp. 3841-3844, Tetrahedron Letters.
M. Murata et al., "Palladium-Catalyzed Borylation of Aryl Halides or Triflates with Dialkoxyborane: A Novel and Facile Synthetic Route to Arylboronates", 2000, vol. 65, pp. 164-168, J. Org. Chem.

(Continued)

*Primary Examiner*—Kamal A Saeed
*Assistant Examiner*—Alicia L Fierro
(74) *Attorney, Agent, or Firm*—Sylvia A. Ayler; William Krovatin

(57) ABSTRACT

Biaryl substituted triazole compounds represented by Formula I, II or III, or pharmaceutically acceptable salts thereof, and a process for making such compounds and salts thereof. Pharmaceutical compositions comprise an effective amount of the instant compounds, either alone, or in combination with one or more other therapeutically active compounds, and a pharmaceutically acceptable carrier. Methods of treating conditions associated with, or caused by, sodium channel activity, including, for example, acute pain, chronic pain, visceral pain, inflammatory pain, neuropathic pain, epilepsy, irritable bowel syndrome, depression, anxiety, multiple sclerosis, and bipolar disorder, comprise administering an effective amount of the present compounds, either alone, or in combination with one or more other therapeutically active compounds. A method of administering local anesthesia comprises administering an effective amount of a compound of the instant invention, either alone, or in combination with one or more other therapeutically active compounds, and a pharmaceutically acceptable carrier.

13 Claims, No Drawings

OTHER PUBLICATIONS

Y. Lin et al., "New Synthesis of 1,2, 4-Triazoles and 1,2,4-Oxadiazoles", 1979, vol. 44, pp. 4160-4164, J. of Organic Chemistry.

G. T. Carter et al., "Advances in the Management of Neuropathic Pain", 2001, vol. 12, pp. 447-459, Pysical Medicine and Rehabilitation Clinics of North America.

Chemical Abstracts, vol. 78, 1973, p. 464, Abstract No. 72013w.

A. Omodei-Sale et al., "A New Class of Nonhormonal Pregancy-Terminating Agents. Synthesis and Contragestational Activity of 3,5-Diaryl-s-Triazoles", 1983, vol. 26, pp. 1187-1192, American Chemical Society.

G. A. Patani et al., "Bioisosterism: A Rational Approach in Drug Design", 1996, vol. 96, pp. 3147-3176, Chem. Rev.

D. Catarzi et al, "Synthesis of Some 2-Aryl-1,2 4-Triazolo[1,5-c][1,3] Benzoxazin-5-Ones as Tools to Define the Essential Pharmacophoric Descriptors of a Benzodiazepine Receptor Ligand", 1995, vol. 38, No. 12, pp. 2196-2201, J. of Medicinal Chemistry.

J. E. Baldwin et al., "Concise Syntheses of acromelic Acid A and Ilo-Acromelic Acid A", 1998, vol. 39, pp. 707-710, Tetrahedron Letters.

* cited by examiner

US 7,572,822 B2

BIARYL SUBSTITUTED TRIAZOLES AS SODIUM CHANNEL BLOCKERS

CROSS REFERENCE TO RELATED APPLICATIONS

This application is a continuation of U.S. patent application Ser. No. 10/779,230, filed Mar. 12, 2004, now U.S. Pat. No. 7,326,726, which claims priority to U.S. Provisional Application 60/455,952, filed Mar. 18, 2003.

FIELD OF THE INVENTION

The present invention is directed to a series of biaryl substituted triazole compounds. In particular, this invention is directed to biaryl substituted triazoles that are sodium channel blockers useful for the treatment of chronic and neuropathic pain. The compounds of the present invention are also useful for the treatment of other conditions, including disorders of the central nervous system (CNS) such as epilepsy, manic depression, bipolar disorder, depression, anxiety and diabetic neuropathy.

BACKGROUND OF THE INVENTION

Voltage-gated ion channels allow electrically excitable cells to generate and propagate action potentials and therefore are crucial for nerve and muscle function. Sodium channels play a special role by mediating rapid depolarization, which constitutes the rising phase of the action potential and in turn activates voltage-gated calcium and potassium channels. Voltage-gated sodium channels represent a multigene family. Nine sodium channel subtypes have been cloned and functionally expressed to date. [Clare, J. J., Tate, S. N., Nobbs, M. & Romanos, M. A. Voltage-gated sodium channels as therapeutic targets. *Drug Discovery Today* 5, 506-520 (2000)]. They are differentially expressed throughout muscle and nerve tissues and show distinct biophysical properties. All voltage-gated sodium channels are characterized by a high degree of selectivity for sodium over other ions and by their voltage-dependent gating. [Catterall, W. A. Structure and function of voltage-gated sodium and calcium channels. *Current Opinion in Neurobiology* 1, 5-13 (1991)]. At negative or hyperpolarized membrane potentials, sodium channels are closed. Following membrane depolarization, sodium channels open rapidly and then inactivate. Sodium channels only conduct currents in the open state and, once inactivated, have to return to the resting state, favored by membrane hyperpolarization, before they can reopen. Different sodium channel subtypes vary in the voltage range over which they activate and inactivate as well as in their activation and inactivation kinetics.

Sodium channels are the target of a diverse array of pharmacological agents, including neurotoxins, antiarrhythmics, anticonvulsants and local anesthetics. [Clare, J. J., Tate, S. N., Nobbs, M. & Romanos, M. A. Voltage-gated sodium channels as therapeutic targets. *Drug Discovery Today* 5, 506-520 (2000)]. Several regions in the sodium channel secondary structure are involved in interactions with these blockers and most are highly conserved. Indeed, most sodium channel blockers known to date interact with similar potency with all channel subtypes. Nevertheless, it has been possible to produce sodium channel blockers with therapeutic selectivity and a sufficient therapeutic window for the treatment of epilepsy (e.g. lamotrigine, phenyloin and carbamazepine) and certain cardiac arrhythmias (e.g. lignocaine, tocamide and mexiletine).

It is well known that the voltage-gated $Na^+$ channels in nerves play a critical role in neuropathic pain. Injuries of the peripheral nervous system often result in neuropathic pain persisting long after the initial injury resolves. Examples of neuropathic pain include, but are not limited to, postherpetic neuralgia, trigeminal neuralgia, diabetic neuropathy, chronic lower back pain, phantom limb pain, pain resulting from cancer and chemotherapy, chronic pelvic pain, complex regional pain syndrome and related neuralgias. It has been shown in human patients as well as in animal models of neuropathic pain, that damage to primary afferent sensory neurons can lead to neuroma formation and spontaneous activity, as well as evoked activity in response to normally innocuous stimuli. [Carter, G. T. and B. S. Galer, *Advances in the management of neuropathic pain*. Physical Medicine and Rehabilitation Clinics of North America, 2001. 12(2): p. 447-459]. The ectopic activity of normally silent sensory neurons is thought to contribute to the generation and maintenance of neuropathic pain. Neuropathic pain is generally assumed to be associated with an increase in sodium channel activity in the injured nerve. [Baker, M. D. and J. N. Wood, *Involvement of Na channels in pain pathways*. TRENDS in Pharmacological Sciences, 2001. 22(1): p. 27-31].

Indeed, in rat models of peripheral nerve injury, ectopic activity in the injured nerve corresponds to the behavioral signs of pain. In these models, intravenous application of the sodium channel blocker and local anesthetic lidocaine can suppress the ectopic activity and reverse the tactile allodynia at concentrations that do not affect general behavior and motor function. [Mao, J. and L. L. Chen, *Systemic lidocaine for neuropathic pain relief*. Pain, 2000. 87: p. 7-17]. These effective concentrations were similar to concentrations shown to be clinically efficacious in humans. [Tanelian, D. L. and W. G. Brose, *Neuropathic pain can be relieved by drugs that are use-dependent sodium channel blockers: lidocaine, carbamazepine and mexiletine*. Anesthesiology, 1991. 74(5): p. 949-951]. In a placebo-controlled study, continuous infusion of lidocaine caused reduced pain scores in patients with peripheral nerve injury, and in a separate study, intravenous lidocaine reduced pain intensity associated with postherpetic neuralgia (PHN). [Mao, J. and L. L. Chen, *Systemic lidocaine for neuropathic pain relief*. Pain, 2000. 87: p. 7-17. Anger, T., et al., *Medicinal chemistry of neuronal voltage-gated sodium channel blockers*. Journal of Medicinal Chemistry, 2001. 44(2): p. 115-137]. Lidoderm®, lidocaine applied in the form of a dermal patch, is currently the only FDA approved treatment for PHN. [Devers, A. and B. S. Galer, *Topical lidocaine patch relieves a variety of neuropathic pain conditions: an open-label study*. Clinical Journal of Pain, 2000. 16(3): p. 205-208].

In addition to neuropathic pain, sodium channel blockers have clinical uses in the treatment of epilepsy and cardiac arrhythmias. Recent evidence from animal models suggests that sodium channel blockers may also be useful for neuroprotection under ischaemic conditions caused by stroke or neural trauma and in patients with multiple sclerosis (MS). [Clare, J. J., et al. And Anger, T., et al.].

International Patent Publication WO 00/57877 describes aryl substituted pyrazoles, imidazoles, oxazoles, thiazoles, and pyrroles and their uses as sodium channel blockers. International Patent Publication WO 01/68612 describes aryl substituted pyridines, pyrimidines, pyrazines and triazines and their uses as sodium channel blockers. International Patent Publication WO 99/32462 describes triazine compounds for the treatment for CNS disorders. However, there remains a need for novel compounds and compositions that therapeutically block neuronal sodium channels with less side effects and higher potency than currently known compounds.

SUMMARY OF THE INVENTION

The present invention is directed to biaryl substituted triazole compounds which are sodium channel blockers useful for the treatment of chronic and neuropathic pain. The compounds of the present invention are also useful for the treatment of other conditions, including disorders of the CNS such as epilepsy, manic depression and bipolar disorder. This invention also provides pharmaceutical compositions comprising a compound of the present invention, either alone, or in combination with one or more therapeutically active compounds, and a pharmaceutically acceptable carrier.

This invention further comprises methods for the treatment of acute pain, chronic pain, visceral pain, inflammatory pain, neuropathic pain and disorders of the CNS including, but not limited to, epilepsy, manic depression, depression, anxiety and bipolar disorder comprising administering the compounds and pharmaceutical compositions of the present invention. The invention also encompasses a process for making the instant compounds.

DETAILED DESCRIPTION OF THE INVENTION

The present invention comprises compounds represented by Formula (I) or (II):

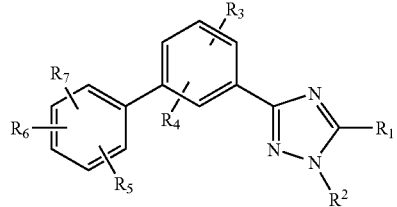
(I)

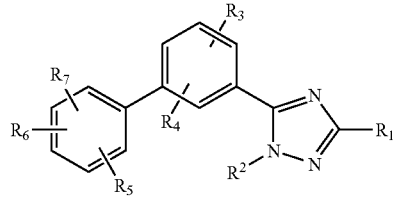
(II)

or pharmaceutically acceptable salts thereof, wherein
$R^1$ is
(a) H;
(b) $C_1$-$C_6$-alkyl, $C_2$-$C_4$-alkenyl, $C_2$-$C_4$-alkynyl, $C_3$-$C_6$-cycloalkyl, or $C_1$-$C_4$-alkyl-[$C_3$-$C_6$-cycloalkyl], any of which is optionally substituted with one or more of the following substituents: F, $CF_3$, OH, O—($C_1$-$C_4$)alkyl, $S(O)_{0-2}$—($C_1$-$C_4$)alkyl, O—$CONR^aR^b$, $NR^aR^b$, $N(R^a)CONR^aR^b$, COO—($C_1$-$C_4$)alkyl, COOH, CN, $CONR^aR^b$, $SO_2NR^aR^b$, $N(R^a)SO_2NR^aR^b$, —C(=NH)$NH_2$, tetrazolyl, triazolyl, imidazolyl, oxazolyl, oxadiazolyl, isooxazolyl, thiazolyl, furyl, thienyl, pyrazolyl, pyrrolyl, pyridyl, pyrimidinyl, pyrazinyl, phenyl, piperidinyl, morpholinyl, pyrrolidinyl or piperazinyl;
(c) —$C_0$-$C_4$-alkyl-$C_1$-$C_4$-perfluoroalkyl;
(d) $NO_2$;
(e) $NR^aR^b$, —$N(COR^a)R^b$, —$N(SO_2R^a)R^b$, —$N(R^a)SO_2R^a$, —$N(OR^a)CONR^aR^b$, —$N(R^a)CON(R^a)_2$, or —$N(R^a)SO_2N(R^a)_2$;

(f) —CH(OR$^a$)R$^a$, —C(OR$^b$)CF$_3$, —CH(NHR$^b$)R$^a$, C(=O)R$^a$, C(=O)CF$_3$, —SOCH$_3$, —SO$_2$CH$_3$, COOR$^a$, CN, CONR$^a$R$^b$, —COCONR$^a$R$^b$, —SO$_2$NR$^a$R$^b$, —CH$_2$O—SO$_2$NR$^a$R$^b$, SO$_2$N(R$^a$)OR$^a$, —C(=NH)NH$_2$, —CR$^a$=N—OR$^a$, CH=CHCONR$^a$R$^b$;
(g) —CONR$^a$(CH$_2$)$_{0-2}$C(R$^a$)(R$^b$)(CH$_2$)$_{0-2}$CONR$^a$R$^b$;
(h) tetrazolyl, tetrazolinonyl, triazolyl, triazolinonyl, imidazolyl, imidozolonyl, oxazolyl, oxadiazolyl, isooxazolyl, thiazolyl, furyl, thienyl, pyrazolyl, pyrazolonyl, pyrrolyl, pyridyl, pyrimidinyl, pyrazinyl, or phenyl, any of which is optionally substituted with 1-3 independent substituents selected from i) F, Cl, Br, I, ii) —CN, iii) —NO$_2$, iv) —C(=O)R$^a$, v) C$_1$-C$_6$-alkyl, vi) —O—R$^a$, vii) —NR$^a$R$^b$, viii) —C$_0$-C$_4$-alkyl —CO—OR$^a$, ix) —(C$_0$-C$_4$-alkyl)-NH—CO—OR$^a$, x) —(C$_0$-C$_4$-alkyl)-CO—NR$^a$R$^b$, xi) —S(O)$_{0-2}$R$^a$, xii) —SO$_2$NR$^a$R$^b$, xiii) —NHSO$_2$R$^a$, xiv) —C$_1$-C$_4$-perfluoroalkyl, and xv) —O—C$_1$-C$_4$-perfluoroalkyl;
(i) —C(R$^a$)=C(R$^b$)—COOR$^a$, or —C(R$^a$)=C(R$^b$)—CONR$^a$R$^b$;

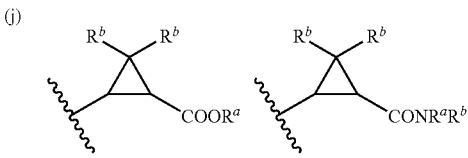
(j)

(k) piperidin-1-yl, morpholin-4-yl, pyrrolidin-1-yl, piperazin-1-yl or 4-substituted piperazin-1-yl, any of which is optionally substituted with 1-3 substituents selected from i) —CN, ii) —C(=O)(R$^a$), iii) C$_1$-C$_6$-alkyl, iv) —OR$^a$, v) —NR$^a$R$^b$, vi) —C$_0$-C$_4$-alkyl-CO—OR$^a$, vii) —(C$_0$-C$_4$-alkyl)-NH—CO—OR$^a$, viii) —(C$_0$-C$_4$-alkyl)-CON(R$^a$)(R$^b$), ix) —SR$^a$, x) —S(O)$_{0-2}$R$^a$, xi) —SO$_2$N(R$^a$)(R$^b$), xii) —NR$^a$SO$_2$R$^a$ xiii) —C$_1$-C$_4$-perfluoroalkyl and xiv) —O—C$_1$-C$_4$-perfluoroalkyl;

$R^a$ is
(a) H;
(b) C$_1$-C$_4$-alkyl, optionally substituted with one or more of the following substituents: F, CF$_3$, OH, O—(C$_1$-C$_4$)alkyl, S(O)$_{0-2}$—(C$_1$-C$_4$)alkyl, —OCONH$_2$, —OCONH(C$_1$-C$_4$alkyl), —OCON(C$_1$-C$_4$alkyl)(C$_1$-C$_4$alkyl), —OCONHC$_1$-C$_4$alkyl-aryl), —OCON(C$_1$-C$_4$alkyl)(C$_1$-C$_4$alkyl-aryl), NH$_2$, NH(C$_1$-C$_4$alkyl), N(C$_1$-C$_4$alkyl)(C$_1$-C$_4$alkyl), NH(C$_1$-C$_4$alkyl-aryl), N(C$_1$-C$_4$alkyl)(C$_1$-C$_4$alkyl-aryl), NHCONH$_2$, NHCONH(C$_1$-C$_4$alkyl), NHCONH(C$_1$-C$_4$alkyl-aryl), —NHCON(C$_1$-C$_4$alkyl)(C$_1$-C$_4$alkyl), NHCON(C$_1$-C$_4$alkyl)(C$_1$-C$_4$alkyl-aryl), N(C$_1$-C$_4$alkyl)CON(C$_1$-C$_4$alkyl)(C$_1$-C$_4$alkyl), N(C$_1$-C$_4$alkyl)CON(C$_1$-C$_4$alkyl)(C$_1$-C$_4$alkyl-aryl), COO—(C$_1$-C$_4$-alkyl), COOH, CN, CONH$_2$, CONH(C$_1$-C$_4$alkyl), CON(C$_1$-C$_4$alkyl)(C$_1$-C$_4$alkyl), SO$_2$NH$_2$, SO$_2$NH(C$_1$-C$_4$alkyl), SO$_2$NH(C$_1$-C$_4$alkyl-aryl), SO$_2$N(C$_1$-C$_4$alkyl)(C$_1$-C$_4$alkyl), NHSO$_2$NH$_2$, —C(=NH)NH$_2$, tetrazolyl, triazolyl, imidazolyl, oxazolyl, oxadiazolyl, isooxazolyl, thiazolyl, furyl, thienyl, pyrazolyl, pyrrolyl, pyridyl, pyrimidinyl, pyrazinyl, phenyl, piperidinyl, morpholinyl, pyrrolidinyl or piperazinyl;
(c) C$_0$-C$_4$-alkyl-(C$_1$-C$_4$)-perfluoroalkyl; or
(d) —C$_1$-C$_4$-alkyl-aryl, wherein aryl is phenyl, pyridyl, pyrimidinyl, furyl, thienyl, pyrrolyl, triazolyl, pyrazolyl, thiazolyl, isoxazolyl, oxazolyl, or oxadiazolyl, any aryl of which is optionally substituted with 1-3 substituents selected from i) F, Cl, Br, I, ii) —CN, iii) —NO$_2$, iv)

—C(═O)($C_1$-$C_4$-alkyl), v) —O($C_1$-$C_4$-alkyl), vi) —N($C_1$-$C_4$-alkyl)($C_1$-$C_4$-alkyl), vii) —$C_{1-10}$alkyl, and viii) —$C_{1-10}$alkyl, wherein one or more of the alkyl carbons can be replaced by a —O—, —S(O)$_{1-2}$—, —O—C(O)—, —C(O)—O—, —C(O)—, —CH(OH)—, —C═C—, or —C≡C—;

$R^b$ is
(a) H; or
(b) $C_1$-$C_6$-alkyl, optionally substituted with one or more of the following substituents: F, CF$_3$, OH, O—($C_1$-$C_4$)alkyl, S(O)$_{0-2}$—($C_1$-$C_4$)alkyl, —OCONH$_2$, —OCONH($C_1$-$C_4$alkyl), NH$_2$, NH($C_1$-$C_4$alkyl), N($C_1$-$C_4$alkyl)($C_1$-$C_4$alkyl), NHCONH$_2$, NHCONH($C_1$-$C_4$alkyl), —NHCON($C_1$-$C_4$alkyl)($C_1$-$C_4$alkyl), COO—($C_1$-$C_4$-alkyl), COOH, CN, or CONH$_2$;

$R^2$ is:
(a) H;
(b) —$C_1$-$C_4$-alkyl, —$C_3$-$C_6$-cycloalkyl or —$C_1$-$C_4$-alkyl-($C_3$-$C_6$)-cycloalkyl, optionally substituted with one or more of the following substituents: F, CF$_3$, OH, O—($C_1$-$C_4$)alkyl, S(O)$_{0-2}$—($C_1$-$C_4$)alkyl, O—CONR$^a$R$^b$, NR$^a$R$^b$, N(R$^a$)CONR$^a$R$^b$, COO—($C_1$-$C_4$)alkyl, COOH, CN, CONR$^a$R$^b$, SO$_2$NR$^a$R$^b$, N(R$^a$R$^b$)SO$_2$NR$^a$R$^b$, —C(═NH)NH$_2$, tetrazolyl, triazolyl, imidazolyl, oxazolyl, oxadiazolyl, isooxazolyl, thiazolyl, furyl, thienyl, pyrazolyl, pyrrolyl, pyridyl, pyrimidinyl, pyrazinyl, phenyl, piperidinyl, morpholinyl, pyrrolidinyl or piperazinyl;
(c) —$C_0$-$C_4$-alkyl-$C_1$-$C_4$-perfluoroalkyl;
(d) aryl or —($C_1$-$C_4$-alkyl)-aryl, wherein aryl is phenyl, pyridyl, pyrimidinyl, furyl, thienyl, pyrrolyl, triazolyl, pyrazolyl, thiazolyl, isoxazolyl, oxazolyl, or oxadiazolyl, any aryl of which is optionally substituted with 1-3 substituents selected from i) F, Cl, Br, I, ii) —CN, iii) —NO$_2$, iv) —C(═O)(R$^a$), v) —OR$^a$, vi) —NR$^a$R$^b$, vii) —$C_{0-4}$alkyl-CO—OR$^a$, viii) —($C_{0-4}$alkyl)-NH—CO—OR$^a$, ix) —($C_{0-4}$alkyl)-CO—N(R$^a$)(R$^b$), x) —S(O)$_{0-2}$R$^a$, xi) —SO$_2$N(R$^a$)(R$^b$), xii) —NR$^a$SO$_2$R$^a$, xiii) —$C_{1-10}$alkyl, and xiv) —$C_{1-10}$alkyl, wherein one or more of the alkyl carbons can be replaced by a —NR$^a$—, —O—, —S(O)$_{1-2}$—, —O—C(O)—, —C(O)—O—, —C(O)—N(R$^a$)—, —N(R$^a$)—C(O)—, —N(R$^a$)—C(O)—N(R$^a$)—, —C(O)—, —CH(OH)—, —C═C—, or —C≡C—;
(e) —C(═O)(R$^a$), —CONR$^a$R$^b$, —COO—($C_1$-$C_4$)alkyl, —SO$_2$R$^a$, —SO$_2$N(R$^a$)(R$^b$);

$R^3$ and $R^4$ each independently is:
(a) H;
(b) —$C_1$-$C_6$-alkyl, —$C_2$-$C_6$-alkenyl, —$C_2$-$C_6$-alkynyl or —$C_3$-$C_6$-cycloalkyl, any of which is optionally substituted with one or more of the following substituents: F, CF$_3$, —O—($C_1$-$C_4$)alkyl, CN, —N(R$^a$)(R$^b$), —N(R$^a$)CO—($C_1$-$C_4$)alkyl, COOR$^b$, CON(R$^a$)(R$^b$) or phenyl;
(c) —O—$C_0$-$C_6$-alkyl, —O-aryl, or —O—$C_1$-$C_4$-alkyl-aryl, wherein aryl is phenyl, pyridyl, pyrimidinyl, furyl, thienyl, pyrrolyl, triazolyl, pyrazolyl, thiazolyl, isoxazolyl, oxazolyl, or oxadiazolyl, any aryl of which is optionally substituted with 1-3 substituents selected from i) F, Cl, Br, I, ii) —CN, iii) —NO$_2$, iv) —C(═O)(R$^a$), v) —OR$^a$, vi) —NR$^a$R$^b$, vii) —$C_{0-4}$alkyl-CO—OR$^a$, viii) —($C_{0-4}$alkyl)-NH—CO—OR$^a$, ix) —($C_{0-4}$alkyl)-CO—N(R$^a$)(R$^b$), x) —S(O)$_{0-2}$R$^a$, xi) —SO$_2$N(R$^a$)(R$^b$), xii) —NR$^a$SO$_2$R$^a$, xiii) —$C_{1-10}$alkyl, and xiv) —$C_{1-10}$alkyl, wherein one or more of the alkyl carbons can be replaced by a —NR$^a$—, —O—, —S(O)$_{1-2}$—, —O—C(O)—, —C(O)—O—, —C(O)—N(R$^a$)—, —N(R$^a$)—C(O)—, —N(R$^a$)—C(O)—N(R$^a$)—, —C(O)—, —CH(OH)—, —C═C—, or —C≡C—;
(d) —$C_0$-$C_4$-alkyl-$C_1$-$C_4$-perfluoroalkyl, or —O—$C_0$-$C_4$-alkyl-$C_1$-$C_4$-perfluoroalkyl; or
(e) CN, NH$_2$, NO$_2$, F, Cl, Br, I, OH, OCON(R$^a$)(R$^b$) O($C_1$-$C_4$-alkyl)CONR$^a$R$^b$, —OSO$_2$N(R$^a$)(R$^b$), COOR$^b$, CON(R$^a$)(R$^b$), or aryl, wherein aryl is phenyl, pyridyl, pyrimidinyl, furyl, thienyl, pyrrolyl, triazolyl, pyrazolyl, thiazolyl, isoxazolyl, oxazolyl, or oxadiazolyl, any aryl of which is optionally substituted with 1-3 substituents selected from i) F, Cl, Br, I, ii) —CN, iii) —NO$_2$, iv) —C(═O)(R$^a$), v) —OR$^a$, vi) —NR$^a$R$^b$, vii) —$C_{0-4}$alkyl-CO—OR$^a$, viii) —($C_{0-4}$alkyl)-NH—CO—OR$^a$, ix) —($C_{0-4}$alkyl)-CO—N(R$^a$)(R$^b$), x) —S(O)$_{0-2}$R$^a$, xi) —SO$_2$N(R$^a$)(R$^b$), xii) —NR$^a$SO$_2$R$^a$, xiii) —$C_{1-10}$alkyl, and xiv) —$C_{1-10}$alkyl, wherein one or more of the alkyl carbons can be replaced by a —NR$^a$—, —O—, —S(O)$_{1-2}$—, —O—C(O)—, —C(O)—O—, —C(O)—N(R$^a$)—, —N(R$^a$)—C(O)—, —N(R$^a$)—C(O)—N(R$^a$)—, —C(O)—, —CH(OH)—, —C═C—, or —C≡C; and $R^5$, $R^6$ and $R^7$ each independently is:
(a) H;
(b) $C_1$-$C_6$-alkyl, $C_2$-$C_4$-alkenyl, $C_2$-$C_4$-alkynyl or $C_3$-$C_6$-cycloalkyl, any of which is optionally substituted with one or more of the following substituents: F, CF$_3$, OH, O—($C_1$-$C_4$)alkyl, OCON(R$^a$)(R$^b$), NR$^a$R$^b$, COOR$^a$, CN, CONR$^a$R$^b$, N(R$^a$R$^b$)CONR$^a$R$^b$, N(R$^a$R$^b$)SO$_2$NR$^a$R$^b$ SO$_2$NR$^a$R$^b$, S(O)$_{0-2}$($C_1$-$C_4$-alkyl), —C(═NH)NH$_2$, tetrazolyl, triazolyl, imidazolyl, oxazolyl, oxadiazolyl, isooxazolyl, thiazolyl, furyl, thienyl, pyrazolyl, pyrrolyl, pyridyl, pyrimidinyl, pyrazinyl, phenyl, piperidinyl, morpholinyl, pyrrolidinyl, or piperazinyl;
(c) —O—$C_1$-$C_6$-alkyl, —O—$C_3$-$C_6$-cycloalkyl, —S—$C_1$-$C_6$-alkyl or —S—$C_3$-$C_6$-cycloalkyl, any of which is optionally substituted with one or more of the following substituents: F, CF$_3$, OH, O—($C_1$-$C_4$)alkyl, NH$_2$, NH($C_1$-$C_4$-alkyl), N($C_1$-$C_4$-alkyl)$_2$, COOH, CN, CONH$_2$, CONH($C_1$-$C_4$-alkyl), CONH($C_1$-$C_4$-alkyl)$_2$, SO$_2$NH$_2$, SO$_2$NH($C_1$-$C_4$-alkyl), tetrazolyl, triazolyl, imidazolyl, oxazolyl, oxadiazolyl, isooxazolyl, thiazolyl, furyl, thienyl, pyrazolyl, pyrrolyl, pyridyl, pyrimidinyl, pyrazinyl, phenyl, piperidinyl, morpholinyl, pyrrolidinyl, or piperazinyl;
(d) —$C_0$-$C_4$-alkyl-$C_1$-$C_4$-perfluoroalkyl, or —O—$C_0$-$C_4$-alkyl-$C_1$-$C_4$-perfluoroalkyl;
(e) —O-aryl, or —O—$C_1$-$C_4$-alkyl-aryl, wherein aryl is phenyl, pyridyl, pyrimidinyl, furyl, thienyl, pyrrolyl, triazolyl, pyrazolyl, thiazolyl, isoxazolyl, oxazolyl, or oxadiazolyl, any aryl of which is optionally substituted with 1-3 substituents selected from i) F, Cl, Br, I, ii) —CN, iii) —NO$_2$, iv) —C(═O)(R$^a$), v) —OR$^a$, vi) —NR$^a$R$^b$, vii) —$C_{0-4}$alkyl-CO—OR$^a$, viii) —($C_{0-4}$-alkyl)-NH—CO—, ix) —($C_{0-4}$alkyl)-CO—N(R$^a$)(R$^b$), x) —S(O)$_{0-2}$R$^a$, xi) —SO$_2$N(R$^a$)(R$^b$), xii) —NR$^a$SO$_2$R$^a$, xiii) —$C_{1-10}$alkyl, and xiv) —$C_{1-10}$alkyl, wherein one or more of the alkyl carbons can be replaced by a —NR$^a$—, —O—, —S(O)$_{1-2}$—, —O—C(O)—, —C(O)—O—, —C(O)—N(R$^a$)—, —N(R$^a$)C(O)—, —N(R$^a$)—C(O)—N(R$^a$)—, —C(O)—, —CH(OH)—, —C═C—, or —C≡C;
(f) CN, N(R$^a$)(R$^b$), NO$_2$, F, Cl, Br, I, —OR$^a$, —SR$^a$, —OCON(R$^a$)(R$^b$), —OSO$_2$N(R$^a$)(R$^b$), COOR$^b$, CON(R$^a$)(R$^b$), —N(R$^a$)CON(R$^a$)(R$^b$), —N(R$^a$)SO$_2$N(R$^a$)(R$^b$), C(OR$^b$)R$^a$, —C(OR$^a$)CF$_3$, C(NHR$^a$)CF$_3$, —C(═O)R$^a$, C(═O)CF$_3$, —SOCH$_3$, —SO$_2$CH$_3$, —NHSO$_2$($C_{1-6}$-alkyl), —NHSO$_2$-aryl, SO$_2$N(R$^a$)(R$^b$), —CH$_2$OSO$_2$N(R$^a$)(R$^b$), SO$_2$N(R$^b$)—OR$^a$, —C(═NH)NH$_2$, —CR$_a$═N—OR$_a$, CH═CH or aryl, wherein aryl is phenyl, pyridyl, pyrimidinyl, furyl, thienyl, pyrrolyl, triazolyl, pyrazolyl, thiazolyl, isoxazolyl, oxazolyl, or oxadiazolyl, any aryl of which is optionally substituted with 1-3 substituents selected from i) F, Cl, Br, I, ii) —CN, iii) —NO$_2$, iv) —C(=O)(R$^a$), v) —OR, vi) —NR$^a$R$^b$, vii) —C$_{0-4}$alkyl-CO—OR$^a$, viii) —(C$_{0-4}$alkyl)-NH—CO—OR$^a$, ix) —(C$_{0-4}$ alkyl)-CO—N(R$^a$)(R$^b$), x) —S(O)$_{0-2}$R$^a$, xi) —SO$_2$N(R$^a$)(R$^b$), xii) —NR$^a$SO$_2$R$^a$, xiii) —C$_{1-10}$alkyl, and xiv) —C$_{1-10}$alkyl, wherein one or more of the alkyl carbons can be replaced by a —NR$^a$—, —O—, —S(O)$_{1-2}$—, —O—C(O)—, —C(O)—O—, —C(O)—N(R$^a$)—, —N(R$^a$)—C(O)—, —N(R$^a$)—C(O)—N(R$^a$)—, —C(O)—, —CH(OH)—, —C=C—, or —C≡C;

with the proviso that when R$^5$ and R$^6$ are present on adjacent carbon atoms, R$^5$ and R$^6$, together with the benzene ring to which they are attached, may form a bicyclic aromatic ring selected from naphthyl, indolyl, quinolinyl, isoquinolinyl, quinoxalinyl, benzofuryl, benzothienyl, benzoxazolyl, benzothiazolyl, and benzimidazolyl, any of which is optionally substituted with 1-4 independent substituents selected from i) halogen, ii) —CN, iii) —NO$_2$, iv) —CHO, v) —O—C$_{1-4}$alkyl, vi) —N(C$_{0-4}$alkyl)(C$_{0-4}$alkyl), vii) —C$_{0-4}$alkyl-CO—O(C$_{0-4}$alkyl), viii) —(C$_{0-4}$alkyl)-NH—CO—O(C$_{0-4}$alkyl), ix) —(C$_{0-4}$alkyl)-CO—N(C$_{0-4}$alkyl)(C$_{0-4}$alkyl), x) —S(C$_{0-4}$alkyl), xi) —S(O)(C$_{1-4}$alkyl), xii) —SO$_2$(C$_{0-4}$alkyl), xiii) —SO$_2$N(C$_{0-4}$alkyl)(C$_{0-4}$alkyl), xiv) —NHSO$_2$(C$_{0-4}$alkyl)(C$_{0-4}$alkyl), xv) —C$_{1-10}$alkyl, and xvi) —C$_{1-10}$alkyl in which one or more of the carbons can be replaced by a —N(C$_{0-6}$alkyl)-, —O—, —S(O)$_{1-2}$—, —O—C(O)—, —C(O)—O—, —C(O)—N(C$_{0-6}$alkyl)-, —N(C$_{0-6}$alkyl)-C(O)—, —N(C$_{0-6}$alkyl)-C(O)—N(C$_{0-6}$alkyl)-, —C(O)—, —CH(OH), —C=C—, or —C≡C—.

The present invention further comprises compounds described by Formula III:

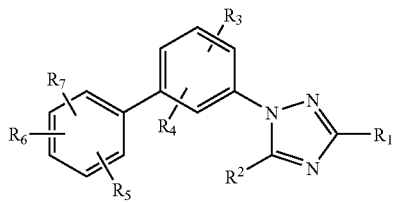

III or pharmaceutical salts thereof, wherein

R$^1$-R$^7$ each is as defined above.

In one aspect, the present invention provides a compound described by the chemical Formula (I), or a pharmaceutically acceptable salt thereof, wherein R$^5$ is other than H and is attached at the ortho position, and all other variables are as previously defined.

In an embodiment of this first aspect, the present invention provides a compound described by the chemical Formula (I), or a pharmaceutically acceptable salt thereof, wherein R$^5$ is —OR$^a$, and all other variables are as previously defined.

In another embodiment of this first aspect, the present invention provides a compound described by the chemical Formula (I), or a pharmaceutically acceptable salt thereof, wherein R$^1$ is optionally substituted C$_1$-C$_6$-alkyl, optionally substituted C$_3$-C$_6$-cycloalkyl, —C(=O)R$^a$ or CONR$^a$R$^b$, and all other variables are as previously defined.

In a second aspect, the present invention provides a compound described by the chemical Formula (II), or a pharmaceutically acceptable salt thereof, wherein R$^5$ is other than H and is attached at the ortho position, and all other variables are as previously defined.

In an embodiment of this second aspect, the present invention provides a compound described by the chemical Formula (II), or a pharmaceutically acceptable salt thereof, wherein R$^5$ is —OR$^a$, and all other variables are as previously defined.

In another embodiment of this second aspect, the present invention provides a compound described by the chemical Formula (II), or a pharmaceutically acceptable salt thereof, wherein R$^1$ is optionally substituted C$_1$-C$_6$-alkyl, optionally substituted C$_3$-C$_6$-cycloalkyl, —C(=O)R$^a$ or CONR$^a$R$^b$, and all other variables are as previously defined.

In a third aspect, the present invention provides a compound described by the chemical Formula (III), or a pharmaceutically acceptable salt thereof, wherein R$^5$ is other than H and is attached at the ortho position, and all other variables are as previously defined.

In an embodiment of this third aspect, the present invention provides a compound described by the chemical Formula (III), or a pharmaceutically acceptable salt thereof, wherein R$^5$ is —OR$^a$, and all other variables are as previously defined.

In another embodiment of this third aspect, the present invention provides a compound described by the chemical Formula (III), or a pharmaceutically acceptable salt thereof, wherein R$^1$ is optionally substituted C$_1$-C$_6$-alkyl, optionally substituted C$_3$-C$_6$-cycloalkyl, —C(=O)R$^a$ or CONR$^a$R$^b$, and all other variables are as previously defined.

In a fourth aspect, the present invention provides compounds described by the chemical Formula (I), which includes compounds of the Formula Ia:

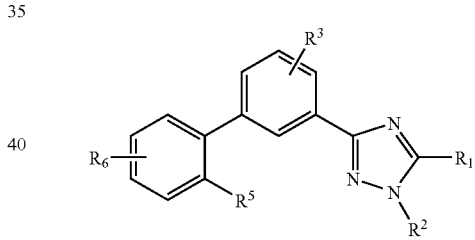

or pharmaceutical acceptable salts thereof, wherein

R$^1$ is optionally substituted C$_1$-C$_6$-alkyl, optionally substituted C$_3$-C$_6$-cycloalkyl, —C(=O)R$^a$ or CONR$^a$R$^b$, R$^5$ is —OR$^a$ or —C$_0$-C$_4$-alkyl-C$_1$-C$_4$-perfluoroalkyl, and all other variables are as previously defined.

The present invention further provides a process for making a compound of Formula (I), or a pharmaceutically acceptable salt thereof, the process comprising reacting a compound of Formula 34 or 35:

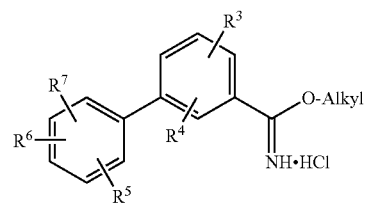

34

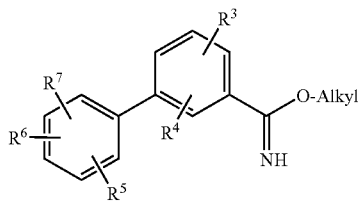

with a compound of Formula 36:

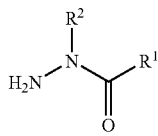

wherein $R^1$-$R^7$ each is as defined above, in the presence of a base to yield a compound of Formula (I), or a pharmaceutically acceptable salt thereof.

In a first aspect of the inventive process, the present invention provides a process for making a compound of Formula (I), or a pharmaceutically acceptable salt thereof, wherein $R^1$ is H, —C(=O)$R^a$, COO$R^a$, CON$R^a R^b$, $C_1$-$C_6$ alkyl or $C_3$-$C_6$ cycloalkyl, wherein alkyl and cycloalkyl is optionally substituted with one or more of F, OH, or N$R^a R^b$, $R^2$ is H, $R^5$, $R^6$ and $R^7$ each independently is H, F, —O$R^a$, $C_1$-$C_6$-alkyl, or —O—$C_1$-$C_6$-alkyl, optionally substituted with one or more of F, CF$_3$, or O—($C_1$-$C_4$)alky, and all other variables are as previously defined.

In a second aspect of the inventive process, the present invention provides a process for making a compound of Formula (I), or a pharmaceutically acceptable salt thereof, wherein the base is a metal acetate, metal carbonate or tertiary amine.

In a third aspect of the inventive process, the present invention provides a process for making a compound of Formula (I), or a pharmaceutically acceptable salt thereof, wherein the base is potassium acetate.

The present invention further provides a process for making a compound of Formula (I), or a pharmaceutically acceptable salt thereof, the process comprising reacting a compound of Formula 34 or 35:

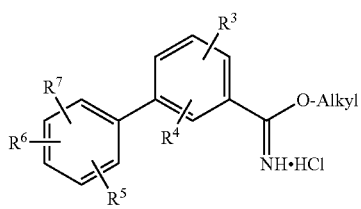

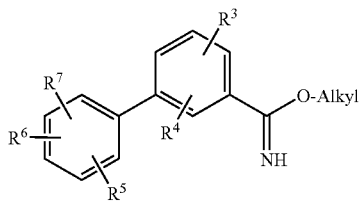

with a compound of Formula 36:

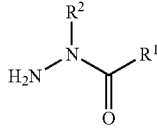

wherein $R^1$-$R^7$ each is as defined above, in the presence of a base, and optionally an alcoholic solvent, and optionally heat, to yield a compound of Formula (I), or a pharmaceutically acceptable salt thereof.

As used herein, "alkyl" as well as other groups having the prefix "alk" such as, for example, alkoxy, alkanoyl, alkenyl, and alkynyl means carbon chains which may be linear or branched or combinations thereof. Examples of alkyl groups include methyl, ethyl, propyl, isopropyl, butyl, sec- and tert-butyl, pentyl, hexyl, and heptyl. "Alkenyl," "alkynyl" and other like terms include carbon chains containing at least one unsaturated C—C bond.

The term "cycloalkyl" means carbocycles containing no heteroatoms, and includes mono-, bi- and tricyclic saturated carbocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ring systems. Examples of cycloalkyl include cyclopropyl, cyclobutyl, cyclopentyl, cyclohexyl, decahydronaphthalene, adamantane, indanyl, indenyl, fluorenyl, and 1,2,3,4-tetrahydronaphalene. Similarly, "cycloalkenyl" means carbocycles containing no heteroatoms and at least one non-aromatic C—C double bond, and include mono-, bi- and tricyclic partially saturated carbocycles, as well as benzofused cycloalkenes. Examples of cycloalkenyl include cyclohexenyl, and indenyl. The term "aryl" includes, but is not limited to, an aromatic substituent that is a single ring or multiple rings fused together. When formed of multiple rings, at least one of the constituent rings is aromatic. The term "aryl", unless specifically noted otherwise, also includes heteroaryls, and thus includes stable 5- to 7-membered monocyclic and stable 9- to 10-membered fused bicyclic heterocyclic ring systems that consist of carbon atoms and from one to four heteroatoms selected from the group consisting of N, O and S, wherein the nitrogen and sulfur heteroatoms may optionally be oxidized, and the nitrogen heteroatom may optionally be quaternized. Suitable aryl groups include phenyl, naphthyl, pyridyl, pyrimidinyl, furyl, thienyl, pyrrolyl, triazolyl, pyrazolyl, thiazolyl, isoxazolyl, oxazolyl, and oxadiazolyl.

The term "cycloalkyloxy," unless specifically stated otherwise, includes a cycloalkyl group connected by a short $C_{1-2}$alkyl to the oxy connecting atom.

The term "$C_{0-6}$alkyl" includes alkyls containing 6, 5, 4, 3, 2, 1, or no carbon atoms. An alkyl with no carbon atoms is a hydrogen atom substituent when the alkyl is a terminal group and is a direct bond when the alkyl is a bridging group.

The term "hetero," unless specifically stated otherwise, includes one or more O, S, or N atoms. For example, heterocycloalkyl and heteroaryl include ring systems that contain one or more O, S, or N atoms in the ring, including mixtures of such atoms. The hetero atoms replace ring carbon atoms. Thus, for example, a heterocyclo$C_5$alkyl is a five-member ring containing from 4 to no carbon atoms. Examples of heteroaryls include pyridinyl, quinolinyl, isoquinolinyl, pyridazinyl, pyrimidinyl, pyrazinyl, quinoxalinyl, furyl, benzofuryl, dibenzofuryl, thienyl, benzthienyl, pyrrolyl, indolyl, pyrazolyl, indazolyl, oxazolyl, benzoxazolyl, isoxazolyl, thiazolyl, benzothiazolyl, isothiazolyl, imidazolyl, benzimidazolyl, oxadiazolyl, thiadiazolyl, triazolyl, and tetrazolyl. Examples of heterocycloalkyls include azetidinyl, pyrrolidinyl, piperidinyl, piperazinyl, morpholinyl, tetrahydrofuranyl, imidazolinyl, pyrrolidin-2-one, piperidin-2-one, and thiomorpholinyl.

The term "hetero$C_{0-4}$alkyl" means a heteroalkyl containing 3, 2, 1, or no carbon atoms. However, at least one heteroatom must be present. Thus, as an example, a hetero$C_{0-4}$alkyl having no carbon atoms but one N atom would be a —NH— if a bridging group and a —NH$_2$ if a terminal group. Analogous bridging or terminal groups are clear for an O or S heteroatom.

The term "amine," unless specifically stated otherwise, includes primary, secondary and tertiary amines.

The term "carbonyl," unless specifically stated otherwise, includes a $C_{0-6}$alkyl substituent group when the carbonyl is terminal.

The term "halogen" includes fluorine, chlorine, bromine and iodine atoms.

The term "optionally substituted" is intended to include both substituted and unsubstituted. Thus, for example, optionally substituted aryl could represent a pentafluorophenyl or a phenyl ring. Further, optionally substituted multiple moieties such as, for example, alkylaryl are intended to mean that the alkyl and the aryl groups are optionally substituted. If only one of the multiple moieties is optionally substituted then it will be specifically recited such as "an alkylaryl, the aryl optionally substituted with halogen or hydroxyl."

As used herein for purposes of the inventive process, the term "base" includes metal acetate bases, metal carbonate bases, and tertiary amine bases. Examples of metal acetate bases include potassium acetate and sodium acetate. Examples of metal carbonate bases include potassium carbonate and sodium carbonate. Tertiary amine bases include trialkyl amine bases such as triethylamine.

As used herein for purposes of the inventive process, the term "alcoholic solvent" or "alcohol solvent" includes, for example, methanol, ethanol, isopropanol and 1-butanol.

Where the inventive process utilizes heat, the process can be carried out in the temperature range of between about 40° C. to about 150° C., including about 50° C. to about 140° C., about 50° C. to about 130° C., about 60° C. to about 120° C., about 65° C. to about 100° C., or about 65° C. to about 85° C.

As used herein, the term "solvent/co-solvent mixture" includes solvent mixtures such as toluene/tetrahydrofuran, tetrahydrofuran/diethylether, toluene/diethylether, tetrahydrofuran/methyl-t-butylether, toluene/methyl-t-butylether, toluene/dioxane, and tetrahydrofuran/dioxane.

Compounds described herein may contain one or more double bonds and may thus give rise to cis/trans isomers as well as other conformational isomers. The present invention includes all such possible isomers as well as mixtures of such isomers unless specifically stated otherwise.

Compounds described herein can contain one or more asymmetric centers and may thus give rise to diastereoisomers and optical isomers. The present invention includes all such possible diastereoisomers as well as their racemic mixtures, their substantially pure resolved enantiomers, all possible geometric isomers, and pharmaceutically acceptable salts thereof. The above chemical Formulas are shown without a definitive stereochemistry at certain positions. The present invention includes all stereoisomers of the chemical Formulas and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, and tromethamine.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. Such additional therapeutic agents can include, for example, i) opiate agonists or antagonists, ii) calcium channel antagonists, iii) 5HT receptor agonists or antagonists, iv) sodium channel antagonists, v) NMDA receptor agonists or antagonists, vi) COX-2 selective inhibitors, vii) NK1 antagonists, viii) non-steroidal anti-inflammatory drugs ("NSAID"), ix) selective serotonin reuptake inhibitors ("SSRI") and/or selective serotonin and norepinephrine reuptake inhibitors ("SSNRI"), x) tricyclic antidepressant drugs, xi) norepinephrine modulators, xii) lithium, xiii) valproate, and xiv) neurontin (gabapentin). The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

The present compounds and compositions are useful for the treatment of chronic, visceral, inflammatory and neuropathic pain syndromes. They are useful for the treatment of pain resulting from traumatic nerve injury, nerve compression or entrapment, postherpetic neuralgia, trigeminal neuralgia, and diabetic neuropathy. The present compounds and compositions are also useful for the treatment of chronic lower back pain, phantom limb pain, chronic pelvic pain, neuroma pain, complex regional pain syndrome, chronic arthritic pain and related neuralgias, and pain associated with cancer, chemotherapy, HIV and HIV treatment-induced neuropathy. Compounds of this invention may also be utilized as local anesthetics. Compounds of this invention are useful for the treatment of irritable bowel syndrome and related disorders, as well as Crohns disease.

The instant compounds have clinical uses for the treatment of epilepsy and partial and generalized tonic seizures. They are also useful for neuroprotection under ischaemic conditions caused by stroke or neural trauma and for treating multiple sclerosis. The present compounds are useful for the treatment of tachy-arrhythmias. Additionally, the instant compounds are useful for the treatment of neuropsychiatric disorders, including mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders;

It will be appreciated that for the treatment of depression or anxiety, a compound of the present invention may be used in conjunction with other anti-depressant or anti-anxiety agents, such as norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), □-adrenoreceptor antagonists, atypical anti-depressants, benzodiazepines, 5-$HT_{1A}$ agonists or antagonists, especially 5-$HT_{1A}$ partial agonists, neurokinin-1 receptor antagonists, corticotropin releasing factor (CRF) antagonists, and pharmaceutically acceptable salts thereof.

Further, it is understood that compounds of this invention can be administered at prophylactically effective dosage levels to prevent the above-recited conditions and disorders, as well as to prevent other conditions and disorders associated with sodium channel activity.

Creams, ointments, jellies, solutions, or suspensions containing the instant compounds can be employed for topical use. Mouth washes and gargles are included within the scope of topical use for the purposes of this invention.

Dosage levels from about 0.01 mg/kg to about 140 mg/kg of body weight per day are useful in the treatment of inflammatory and neuropathic pain, or alternatively about 0.5 mg to about 7 g per patient per day. For example, inflammatory pain may be effectively treated by the administration of from about 0.01 mg to about 75 mg of the compound per kilogram of body weight per day, or alternatively about 0.5 mg to about 3.5 g per patient per day. Neuropathic pain may be effectively treated by the administration of from about 0.01 mg to about 125 mg of the compound per kilogram of body weight per day, or alternatively about 0.5 mg to about 5.5 g per patient per day.

The amount of active ingredient that may be combined with the carrier materials to produce a single dosage form will vary depending upon the host treated and the particular mode of administration. For example, a formulation intended for the oral administration to humans may conveniently contain from about 0.5 mg to about 5 g of active agent, compounded with an appropriate and convenient amount of carrier material which may vary from about 5 to about 95 percent of the total composition. Unit dosage forms will generally contain between from about 1 mg to about 1000 mg of the active ingredient, typically 25 mg, 50 mg, 100 mg, 200 mg, 300 mg, 400 mg, 500 mg, 600 mg, 800 mg or 1000 mg.

It is understood, however, that the specific dose level for any particular patient will depend upon a variety of factors. Such patient-related factors include the age, body weight, general health, sex, and diet of the patient. Other factors include the time and route of administration, rate of excretion, drug combination, and the severity of the particular disease undergoing therapy.

In practice, the compounds of the invention or pharmaceutically acceptable salts thereof, can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention or pharmaceutically acceptable salts thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt of the present compounds. The compounds of the invention, or pharmaceutically acceptable salts thereof, can also be included in pharmaceutical compositions in combination with one or more therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars, microcrystalline cellulose, diluents, granulating agents, lubricants, binders, and disintegrating agents can be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient. Thus, a tablet, cachet, or capsule conveniently contains 0.1 mg, 1 mg, 5 mg, 25 mg, 50 mg, 100 mg, 200 mg, 300 mg, 400 mg, or 500 mg of the active ingredient taken one or two tablets, cachets, or capsules, once, twice, or three times daily.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage, and thus should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, and dusting powder. Further, the compositions can be in a form suitable for use in transdermal devices. These formulations may be prepared, utilizing a compound of the instant invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid, such as, for example, where the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, and preservatives (including anti-oxidants). Furthermore, other adjuvants can be included to render the formulation isotonic with the blood of the intended recipient. Compositions containing a compound of the present invention, or pharmaceutically acceptable salts thereof, can also be prepared in powder or liquid concentrate form.

The compounds and pharmaceutical compositions of this invention have been found to block sodium channels. Accordingly, an aspect of the invention is the treatment in mammals of maladies that are amenable to amelioration through blockage of neuronal sodium channels, including, for example, acute pain, chronic pain, visceral pain, inflammatory pain, and neuropathic pain by administering an effective amount of a compound of this invention. The term "mammals" includes humans, as well as other animals, such as, for example, dogs, cats, horses, pigs, and cattle. Accordingly, it is understood that the treatment of mammals other than humans refers to the treatment of clinical conditions in non-human mammals that correlate to the above-recited conditions.

Further, as described above, the instant compounds can be utilized in combination with one or more therapeutically active compounds. In particular, the inventive compounds can be advantageously used in combination with i) opiate agonists or antagonists, ii) calcium channel antagonists, iii) 5HT receptor agonists or antagonists, iv) sodium channel antagonists, v) N-methyl-D-aspartate (NMDA) receptor agonists or antagonists, vi) COX-2 selective inhibitors, vii) neurokinin receptor 1 (NK1) antagonists, viii) non-steroidal anti-inflammatory drugs (NSAID), ix) selective serotonin reuptake inhibitors (SSRI) and/or selective serotonin and norepinephrine reuptake inhibitors (SSNRI), x) tricyclic antidepressant drugs, xi) norepinephrine modulators, xii) lithium, xiii) valproate, and xiv) neurontin (gabapentin).

The abbreviations used herein have the following tabulated meanings. Abbreviations not tabulated below have their meanings as commonly used unless specifically stated otherwise.

| | |
|---|---|
| Ac | Acetyl |
| AIBN | 2,2'-azobis(isobutyronitrile) |
| BINAP | 1,1'-bi-2-naphthol |
| Bn | Benzyl |
| CAMP | cyclic adenosine-3',5'-monophosphate |
| DAST | (diethylamino)sulfur trifluoride |
| DEAD | diethyl azodicarboxylate |
| DBU | 1,8-diazabicyclo[5.4.0]undec-7-ene |
| DIBAL | diisobutylaluminum hydride |
| DMAP | 4-(dimethylamino)pyridine |
| DMF | N,N-dimethylformamide |
| Dppf | 1,1'-bis(diphenylphosphino)-ferrocene |
| EDCI | 1-(3-dimethylaminopropyl)-3-ethylcarbodiimide hydrochloride |
| Et$_3$N | Triethylamine |
| GST | glutathione transferase |
| HMDS | Hexamethyldisilazide |
| LDA | lithium diisopropylamide |
| m-CPBA | metachloroperbenzoic acid |
| MMPP | monoperoxyphthalic acid |
| MPPM | monoperoxyphthalic acid, magnesium salt 6H$_2$O |

-continued

| | |
|---|---|
| Ms | methanesulfonyl = mesyl = SO$_2$Me |
| MsO | methanesulfonate = mesylate |
| NBS | N-bromo succinimide |
| NSAID | non-steroidal anti-inflammatory drug |
| o-Tol | ortho-tolyl |
| OXONE ® | 2KHSO$_5$•KHSO$_4$•K$_2$SO$_4$ |
| PCC | pyridinium chlorochromate |
| Pd$_2$(dba)$_3$ | Bis(dibenzylideneacetone) palladium(0) |
| PDC | pyridinium dichromate |
| PDE | Phosphodiesterase |
| Ph | Phenyl |
| Phe | Benzenediyl |
| PMB | para-methoxybenzyl |
| Pye | Pyridinediyl |
| r.t. or RT | room temperature |
| Rac. | Racemic |
| SAM | aminosulfonyl or sulfonamide or SO$_2$NH$_2$ |
| SEM | 2-(trimethylsilyl)ethoxymethoxy |
| SPA | scintillation proximity assay |
| TBAF | tetra-n-butylammonium fluoride |
| Th | 2- or 3-thienyl |
| TFA | trifluoroacetic acid |
| TFAA | trifluoroacetic acid anhydride |
| THF | Tetrahydrofuran |
| Thi | Thiophenediyl |
| TLC | thin layer chromatography |
| TMS-CN | trimethylsilyl cyanide |
| TMSI | trimethylsilyl iodide |
| Tz | 1H (or 2H)-tetrazol-5-yl |
| XANTPHOS | 4,5-Bis-diphenylphosphanyl-9,9-dimethyl-9H-xanthene |
| C$_3$H$_5$ | Allyl |

Alkyl Group Abbreviations

| | |
|---|---|
| Me = | Methyl |
| Et = | ethyl |
| n-Pr = | normal propyl |
| i-Pr = | isopropyl |
| n-Bu = | normal butyl |
| i-Bu = | isobutyl |
| s-Bu = | secondary butyl |
| t-Bu = | tertiary butyl |
| c-Pr = | cyclopropyl |
| c-Bu = | cyclobutyl |
| c-Pen = | cyclopentyl |
| c-Hex = | cyclohexyl |

The following in vitro and in vivo assays were used in assessing the biological activity of the instant compounds.

Compound Evaluation (In Vitro Assay):

The identification of inhibitors of the sodium channel is based on the ability of sodium channels to cause cell depolarization when sodium ions permeate through agonist-modified channels. In the absence of inhibitors, exposure of an agonist-modified channel to sodium ions will cause cell depolarization. Sodium channel inhibitors will prevent cell depolarization caused by sodium ion movement through agonist-modified sodium channels. Changes in membrane potential can be determined with voltage-sensitive fluorescence resonance energy transfer (FRET) dye pairs that use two components, a donor coumarin (CC$_2$DMPE) and an acceptor oxanol (DiSBAC$_2$(3)). Oxanol is a lipophilic anion and distributes across the membrane according to membrane potential. In the presence of a sodium channel agonist, but in the absence of sodium, the inside of the cell is negative with respect to the outside, oxanol is accumulated at the outer leaflet of the membrane and excitation of coumarin will cause FRET to occur. Addition of sodium will cause membrane depolarization leading to redistribution of oxanol to the inside of the cell, and, as a consequence, to a decrease in FRET. Thus, the ratio change (donor/acceptor) increases after membrane depolarization. In the presence of a sodium channel inhibitor, cell depolarization will not occur, and therefore the distribution of oxanol and FRET will remain unchanged.

Cells stably transfected with the PN1 sodium channel (HEK-PN1) were grown in polylysine-coated 96-well plates at a density of ca. 140,000 cells/well. The media was aspirated, and the cells were washed with PBS buffer, and incubated with 100 Ml of 10 Mm CC$_2$-DMPE in 0.02% pluronic acid. After incubation at 25° C. for 45 min, media was removed and cells were washed 2× with buffer. Cells were incubated with 100 Ml of DiSBAC$_2$(3) in TMA buffer containing 20 Mm veratridine, 20 Nm brevetoxin-3, and test sample. After incubation at 25° C. for 45 min in the dark, plates were placed in the VIPR instrument, and the fluorescence emission of both CC$_2$-DMPE and DiSBAC$_2$(3) recorded for 10 s. At this point, 100 Ml of saline buffer was added to the wells to determine the extent of sodium-dependent cell depolarization, and the fluorescence emission of both dyes recorded for an additional 20 s. The ratio CC$_2$-DMPE/DiSBAC$_2$(3), before addition of saline buffer equals 1. In the absence of inhibitors, the ratio after addition of saline buffer is >1.5. When the sodium channel has been completely inhibited by either a known standard or test compound, this ratio remains at 1. It is possible, therefore, to titrate the activity of a sodium channel inhibitor by monitoring the concentration-dependent change in fluorescence ratio.

Electrophysiological Assays (In Vitro Assays):

Cell preparation: A HEK-293 cell line stably expressing the PN1 sodium channel subtype was established in-house. The cells were cultured in MEM growth media (Gibco) with 0.5 mg/Ml G418, 50 units/Ml Pen/Strep and 1 Ml heat-inactivated fetal bovine serum at 37° C. and 10% CO$_2$. For electrophysiological recordings, cells were plated on 35 mm dishes coated with poly-D-lysine.

Whole-cell recordings: HEK-293 cells stably expressing the PN1 sodium channel subtype were examined by whole cell voltage clamp (Hamill, et al. Pfluegers Archives 391:85-100 (1981)) using an EPC-9 amplifier and Pulse software (HEKA Electronics, Lamprecht, Germany). Experiments were performed at room temperature. Electrodes were fire-polished to resistances of 2-4 MΩ. Voltage errors were minimized by series resistance compensation, and the capacitance artifact was canceled using the EPC-9's built-in circuitry. Data were acquired at 50 kHz and filtered at 7-10 kHz. The bath solution consisted of 40 mM NaCl, 120 mM NMDG Cl, 1 mM KCl, 2.7 mM CaCl$_2$, 0.5 mM MgCl$_2$, 10 mM NMDG HEPES, Ph 7.4, and the internal (pipet) solution contained 110 mM Cs-methanesulfonate, 5 mM NaCl, 20 mM CsCl, 10 mM CsF, 10 mM BAPTA (tetra Cs salt), 10 mM Cs HEPES, Ph 7.4.

The following protocols were used to estimate the steady-state affinity of compounds for the resting and inactivated state of the channel ($K_r$ and $K_i$, respectively):

1. 8 ms test-pulses to depolarizing voltages from −60 Mv to +50 Mv from a holding potential of −90 Mv were used to construct current-voltage relationships (IV-curves). A voltage near the peak of the IV-curve (typically −10 or 0 Mv) was used as the test-pulse voltage throughout the remainder of the experiment.

2. Steady-state inactivation (availability) curves were constructed by measuring the current activated during an 8 ms test-pulse following 10 s conditioning pulses to potentials ranging from −120 Mv to −10 Mv.

3. Compounds were applied at a holding potential at which 20-50% of the channels was inactivated and sodium channel blockage was monitored during 8 ms test pulses at 2 s intervals.

4. After the compounds equilibrated, the voltage-dependence of steady-state inactivation in the presence of compound was determined according to protocol 2) above. Compounds that block the resting state of the channel decrease the current elicited during test-pulses from all holding potentials, whereas compounds that primarily block the inactivated state shift the mid-point of the steady-state inactivation curve. The maximum current at negative holding potentials ($I_{max}$) and the difference in the mid-points of the steady-state inactivation curves ($\Delta V$) in control and in the presence of a compound were used to calculate $K_r$ and $K_i$ using the following equations:

$$K_r = \frac{[Drug] * I_{Max,Drug}}{I_{Max,Control} - I_{Max,Drug}}$$

$$K_i = \frac{[Drug]}{\left(1 + \frac{[Drug]}{K_r}\right) * e^{\frac{-\Delta V}{k}} - 1}$$

In cases where the compound did not affect the resting state, $K_i$ was calculated using the following equation:

$$K_i = \frac{[Drug]}{e^{\frac{-\Delta V}{k}} - 1}$$

Rat Formalin Paw Test (In Vivo Assay):

Compounds were assessed for their ability to inhibit the behavioral response evoked by a 50 Ml injection of formalin (5%). A metal band was affixed to the left hind paw of male Sprague-Dawley rats (Charles River, 200-250 g) and each rat was conditioned to the band for 60 min within a plastic cylinder (15 cm diameter). Rats were dosed with either vehicle or a test compound either before (local) or after (systemic) formalin challenge. For local administration, compounds were prepared in a 1:4:5 vehicle of ethanol, PEG400 and saline (EPEGS) and injected subcutaneously into the dorsal surface of the left hind paw 5 min prior to formalin. For systemic administration, compounds were prepared in either a EPEGS vehicle or a Tween 80 (10%)/sterile water (90%) vehicle and were injected i.v. (via the lateral tail vein 15 min after formalin) or p.o. (60 min before formalin). The number of flinches was counted continuously for 60 min using an automated nociception analyzer (UCSD Anesthesiology Research, San Diego, Calif.). Statistical significance was determined by comparing the total flinches detected in the early (0-10 min) and late (11-60 min) phase with an unpaired t-test.

In Vivo Assay Using Rat CFA Model:

Unilateral inflammation was induced with a 0.2 ml injection of complete Freund's adjuvant (CFA: Mycobacterium tuberculosis, Sigma; suspended in an oil/saline (1:1) emulsion; 0.5 mg Mycobacterium/Ml) in the plantar surface of the left hindpaw. This dose of CFA produced significant hind paw swelling but the animals exhibited normal grooming behavior and weight gain over the course of the experiment. Mechanical hyperalgesia was assessed 3 days after tissue injury using a Randall-Selitto test. Repeated Measures ANOVA, followed by Dunnett's Post Hoc test.

SNL: Mechanical Allodynia (In Vivo Assay):

Tactile allodynia was assessed with calibrated von Frey filaments using an up-down paradigm before and two weeks following nerve injury. Animals were placed in plastic cages with a wire mesh floor and allowed to acclimate for 15 min before each test session. To determine the 50% response threshold, the von Frey filaments (over a range of intensities from 0.4 to 28.8 g) were applied to the mid-plantar surface for 8 s, or until a withdrawal response occurred. Following a positive response, an incrementally weaker stimulus was tested. If there was no response to a stimulus, then an incrementally stronger stimulus was presented. After the initial threshold crossing, this procedure was repeated for four stimulus presentations per animal per test session. Mechanical sensitivity was assessed 1 and 2 hr post oral administration of the test compound.

The compounds described in this invention displayed sodium channel blocking activity of from about <0.1 mM to about <50 mM in the in vitro assays described above. It is advantageous that the compounds display sodium channel blocking activity of <5 mM in the in vitro assays. It is more advantageous that the compounds display sodium channel blocking activity of <1 mM in the in vitro assays. It is even more advantageous that the compounds display sodium channel blocking activity of <0.5 mM in the in vitro assays. It is still more advantageous that the compounds display sodium channel blocking activity of <0.1 mM in the in vitro assays.

The present compounds can be prepared according to the general Schemes provided below as well as the procedures provided in the Examples. The following Schemes and Examples further describe, but do not limit, the scope of the invention.

Unless specifically stated otherwise, the experimental procedures were performed under the following conditions: All operations were carried out at room or ambient temperature; that is, at a temperature in the range of 18-25° C. Evaporation of solvent was carried out using a rotary evaporator under reduced pressure (600-4000 pascals: 4.5-30 mm. Hg) with a bath temperature of up to 60° C. The course of reactions was followed by thin layer chromatography (TLC) and reaction times are given for illustration only. Melting points are uncorrected and 'd' indicates decomposition. The melting points given are those obtained for the materials prepared as described. Polymorphism may result in isolation of materials with different melting points in some preparations. The structure and purity of all final products were assured by at least one of the following techniques: TLC, mass spectrometry, nuclear magnetic resonance (NMR) spectrometry or microanalytical data. When given, yields are for illustration only. When given, NMR data is in the form of delta ($\delta$) values for major diagnostic protons, given in parts per million (ppm) relative to tetramethylsilane (TMS) as internal standard, determined at 300 MHz, 400 MHz or 500 MHz using the indicated solvent. Conventional abbreviations used for signal shape are: s. singlet; d. doublet; t. triplet; m. multiplet; br. Broad; etc. In addition, "Ar" signifies an aromatic signal. Chemical symbols have their usual meanings; the following abbreviations are used: v (volume), w (weight), b.p. (boiling point), m.p. (melting point), L (liter(s)), ml (milliliters), g (gram(s), mg (milligrams(s), mol (moles), mmol (millimoles), eq (equivalent(s).

Methods of Synthesis

Compounds of the present invention can be prepared according to the Schemes provided below as well as the procedures provided in the Examples. The substituents are the same as in the above Formulas except where defined otherwise or otherwise apparent to the ordinary skilled artisan.

The novel compounds of the present invention can be readily synthesized using techniques known to those skilled in the art, such as those described, for example, in *Advanced Organic Chemistry*, March, 4$^{th}$ Ed., John Wiley and Sons, New York, N.Y., 1992; *Advanced Organic Chemistry*, Carey and Sundberg, Vol. A and B, 3$^{rd}$ Ed., Plenum Press, Inc., New York, N.Y., 1990; *Protective groups in Organic Synthesis*, Green and Wuts, 2$^{nd}$ Ed., John Wiley and Sons, New York, N.Y., 1991; *Comprehensive Organic Transformations*, Larock, VCH Publishers, Inc., New York, N.Y., 1988; *Handbook of Heterocyclic Chemistry*, Katritzky and Pozharskii, 2$^{nd}$ Ed., Pergamon, New York, N.Y., 2000 and references cited therein. The starting materials for the present compounds may be prepared using standard synthetic transformations of chemical precursors that are readily available from commercial sources, including Aldrich Chemical Co. (Milwaukee, Wis.); Sigma Chemical Co. (St. Louis, Mo.); Lancaster Synthesis (Windham, N.H.); Ryan Scientific (Columbia, S.C.); Maybridge (Cornwall, UK); Matrix Scientific (Columbia, S.C.); Arcos, (Pittsburgh, Pa.) and Trans World Chemicals (Rockville, Md.).

The procedures described herein for synthesizing the compounds may include one or more steps of protecting group manipulations and of purification, such as, recrystallization, distillation, column chromatography, flash chromatography, thin-layer chromatography (TLC), radial chromatography and high-pressure chromatography (HPLC). The products can be characterized using various techniques well known in the chemical arts, including proton and carbon-13 nuclear magnetic resonance ($^1$H and $^{13}$C NMR), infrared and ultraviolet spectroscopy (IR and UV), X-ray crystallography, elemental analysis and HPLC and mass spectrometry (LC-MS). Methods of protecting group manipulation, purification, structure identification and quantification are well known to one skilled in the art of chemical synthesis.

Appropriate solvents are those which will at least partially dissolve one or all of the reactants and will not adversely interact with either the reactants or the product. Suitable solvents are aromatic hydrocarbons (e.g, toluene, xylenes), halogenated solvents (e.g, methylene chloride, chloroform, carbontetrachloride, chlorobenzenes), ethers (e.g. diethyl ether, diisopropylether, tert-butyl methyl ether, diglyme, tetrahydrofuran, dioxane, anisole), nitriles (e.g. acetonitrile, propionitrile), ketones (e.g. 2-butanone, dithyl ketone, tert-butyl methyl ketone), alcohols (e.g. methanol, ethanol, n-propanol, iso-propanol, n-butanol, t-butanol), dimethyl formamide (DMF), dimethylsulfoxide (DMSO) and water. Mixtures of two or more solvents can also be used. Suitable bases are, generally, alkali metal hydroxides, alkaline earth metal hydroxides such as lithium hydroxide, sodium hydroxide, potassium hydroxide, barium hydroxide, and calcium hydroxide; alkali metal hydrides and alkaline earth metal hydrides such as lithium hydride, sodium hydride, potassium hydride and calcium hydride; alkali metal amides such as lithium amide, sodium amide and potassium amide; alkali metal carbonates and alkaline earth metal carbonates such as lithium carbonate, sodium carbonate, Cesium carbonate, sodium hydrogen carbonate, and cesium hydrogen carbonate; alkali metal alkoxides and alkaline earth metal alkoxides such as sodium methoxide, sodium ethoxide, potassium tert-butoxide and magnesium ethoxide; alkali metal alkyls such as methyllithium, n-butyllithium, sec-butyllithium, t-bultyllithium, phenyllithium, alkyl magnesium halides, organic bases such as trimethylamine, triethylamine, triisopropylamine, N,N-diisopropylethylamine, piperidine, N-methyl piperidine, morpholine, N-methyl morpholine, pyridine, collidines, lutidines, and 4-dimethylaminopyridine; and bicyclic amines such as DBU and DABCO.

As described previously, in preparing the compositions for oral dosage form, any of the usual pharmaceutical media can be employed. For example, in the case of oral liquid preparations such as suspensions, elixirs and solutions, water, glycols, oils, alcohols, flavoring agents, preservatives, coloring agents and the like may be used; or in the case of oral solid preparations such as powders, capsules and tablets, carriers such as starches, sugars, microcrystalline cellulose, diluents, granulating agents, lubricants, binders, disintegrating agents, and the like may be included. Because of their ease of administration, tablets and capsules represent the most advantageous oral dosage unit form in which solid pharmaceutical carriers are employed. If desired, tablets may be coated by standard aqueous or nonaqueous techniques. In addition to the common dosage forms set out above, controlled release means and/or delivery devices may also be used in administering the instant compounds and compositions.

It is understood that the functional groups present in compounds described in the Schemes below can be further manipulated, when appropriate, using the standard functional group transformation techniques available to those skilled in the art, to provide desired compounds described in this invention.

Other variations or modifications, which will be obvious to those skilled in the art, are within the scope and teachings of this invention. This invention is not to be limited except as set forth in the following claims.

Scheme 1:

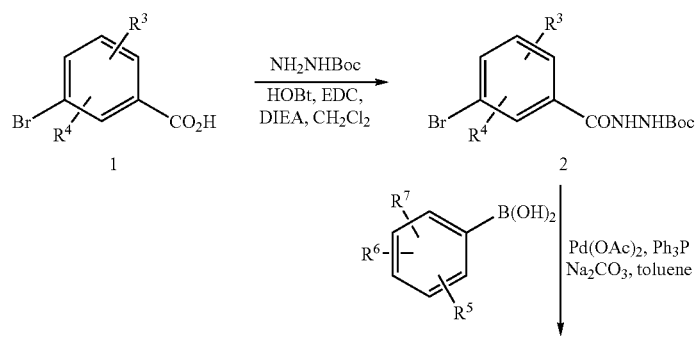

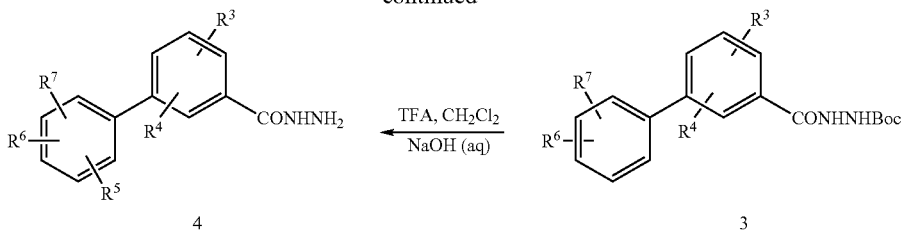

In one protocol, 3-bromobenzoic acid 1 is coupled with t-butyl carbazate by activation with HOBt (hydroxybenzotriazole) in the presence of a suitable carbodiimide such as EDC [1-(3-dimethylaminopropyl)-3-ethylcarbodiimide) and diisopropylethylamine (DIEA) in dichloromethane or THF to give the protected hydrazide 2. There are numerous other iodides and trifluoromethane sulfonates using the method described by Murata, M., et al. [J. Org. Chem. 65: 164-168 (2000)]. The Boc protecting group of compound 3 is removed by standard conditions—trifluoroacetic acid in dichloromethane—to give the TFA salt of hydrazide 4 which can be desalted with aqueous NaOH solution.

Scheme 2:

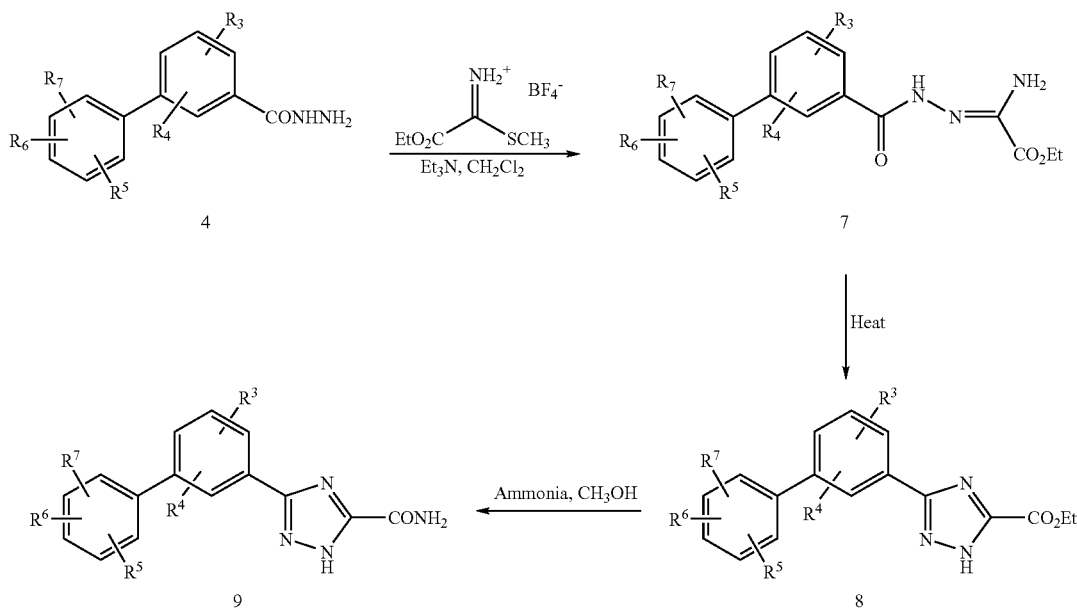

suitable methods to activate carboxylic acids for coupling formation (see March J. "Advanced Organic Chemistry", 5th ed., John Wiley & Sons, New York, pp. 506-512 (2001). Compound 2 can be converted to a variety of unsymmetrical biphenyl intermediates 3 by means of a variety of coupling reactions. One type is the Suzuki reaction wherein bromo, iodo, or triflate compound 2 is reacted with an aryl boronic acid in the presence of a palladium catalyst such as palladium acetate with triphenyl phosphine and aqueous sodium carbonate in a solvent such as toluene and a co-solvent such as n-propanol. (see Suzuki, et al. Chem. Rev., 95, 2457, 1995). A variety of aryl boronic acids are commercially available or can be prepared conveniently from the corresponding aryl bromide or iodide by converting it to an organolithium derivative [Baldwin, J. E., et al. Tetrahedron Lett. 39, 707-710 (1998)], or a Grignard reagent followed by treatment with trialkylborate [Li, J. J. et al, J. Med. Chem, 38: 4570-4578 (1995) and Piettre, S. R., et al. J. Med Chem. 40, 4208-4221 (1997)]. Aryl boronates can also be used as an alternative to aryl boronic acids in these Pd-catalyzed coupling reactions [Giroux, A., et al., Tetrahedron Lett., 38, 3841 (1997)]. The boronates can be easily prepared from the aryl bromides, In Scheme 2, a method is described for preparing 5-biphenyl-3-substituted-1,2,4-triazole derivatives wherein the substitution can be esters, acids, amides, etc. (Catarzi, et al. J. Med. Chem., 38, 2196-2201, 1995). Reaction of hydrazide 4 with carbethoxy-5-methyl-thioformimidium tetrafluoroborate and triethylamine in dichloromethane gives oxamidrazonate 7 which is cyclized to triazole ester 8. The reagent carbethoxy-S-methyl-thioformimidium tetrafluoroborate is prepared by reaction of ethyl-2-thiooxamate with trimethyl oxonium tetrafluoroborate (see Catarzi, et al. above) in dichloromethane. Ester 8 can be converted to an amide by heating it with the corresponding amine, in this case ammonia, in a solvent such as methanol. Ester 8 can be hydrolyzed to the corresponding acid under standard conditions, and the resulting acid can be converted to an amide under a variety of conditions such as those described in Scheme 1. Additionally, ester 8 can be reduced to a primary alcohol with, for example, sodium borohydride (NaBH$_4$), to provide compounds of Formula (I) wherein $R^1$ is hydroxymethyl. Alternatively, ester 8 can be converted to a secondary alcohol by reaction with a mixture of lithium borohydride and a Grignard reagent in an aprotic solvent such as THF. Such primary or secondary alcohol derived from ester 8 can be further derivatized by a number of methods, including oxidation to a ketone by an oxidizing reagent such as a chromium-based reagent. Such alcohol can also be converted to a fluoride derivative by, for example, reaction with diethylaminosulfurtrifluoride (DAST) in dichlormethane at reduced temperatures.

give biphenylester 11. The ester 11 provides a preformed biphenyl intermediate that can be further elaborated to compound 4 and related derivatives as described in earlier Schemes 1-2. In this Scheme 3, ester 11 is converted to amide 12 under standard conditions. Specifically, ester 11 is hydrolyzed to the corresponding acid which is then activated with carbonyldiimidazole (CDI) in DMF, followed by the addition

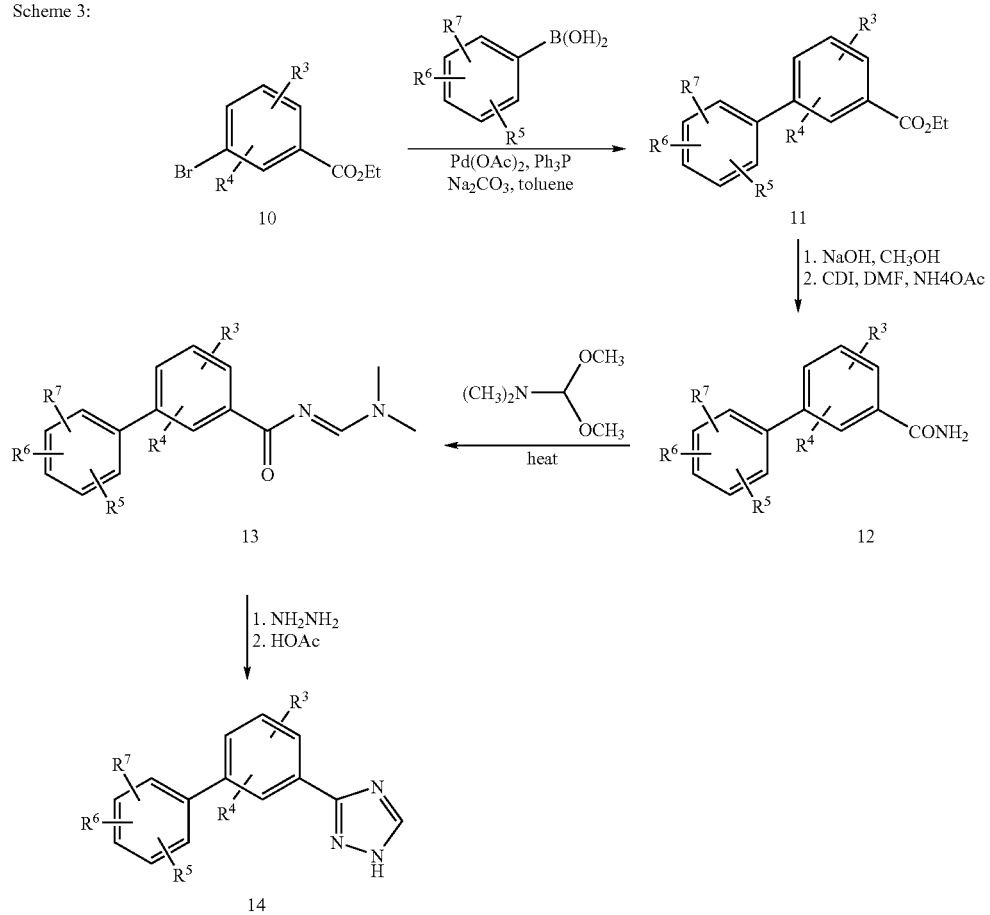

In Scheme 3, a method is described for preparing an unsubstituted 3-triazole ring system (Lin, et al, *J. Org. Chem.*, 44(23), 4160-4165, 1979). Ethyl-3-bromobenzoate 10 is reacted with an aryl boronic acid as described in Scheme 1 to of ammonia in the form of ammonium acetate to give amide 12. Amide 12 in dimethylformamide dimethylacetal is heated to give intermediate 13 which, when heated with hydrazine in acetic acid, gives triazole 14.

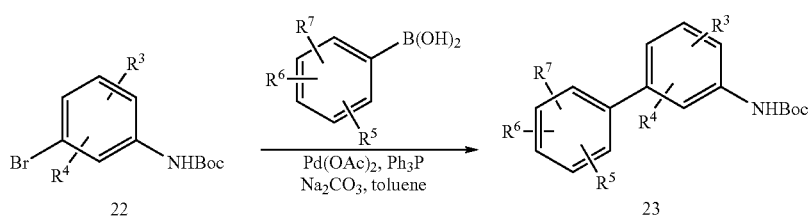

-continued

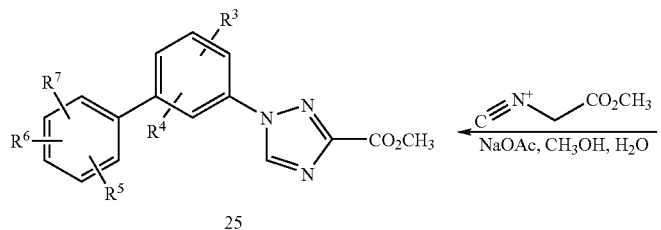

25

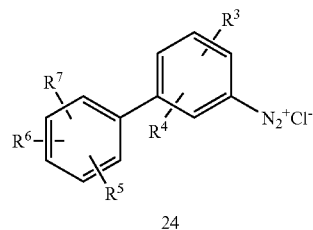

24

-continued

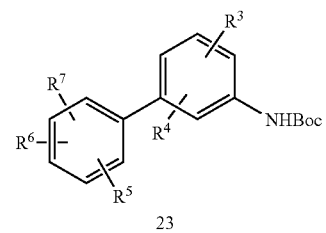

23

In a protocol to prepare 1-biphenyl-3-substituted-1,2,4-triazole derivatives, bromoaniline 22, wherein the amino group is protected with a Boc group, and an arylboronic acid is converted to a variety of unsymmetrical biphenyl intermediates 23 as described in Scheme 1. The Boc protecting group of compound 23 is removed as described previously and converted to its diazonium salt 24 by standard reaction with sodium nitrite and HCl in water. Addition of compound 24 to a mixture of methylisocyanoacetate and sodium acetate in methanol and water gave the triazole ester 25. The key intermediate 25 can be then converted to a variety of useful derivatives using the methods described in Schemes 1-3.

Scheme 5:

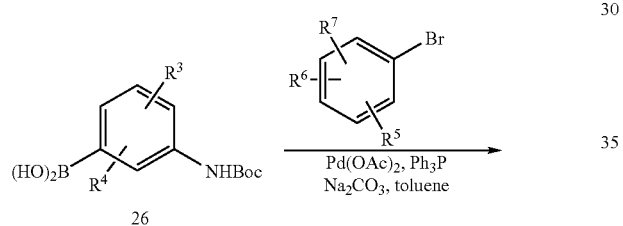

26

In a variation to the protocols described in Schemes 1, 3 and 4 above, the Boc-protected aniline 26 containing a boronic acid group or boronate ester and an aryl bromide, iodide or triflate is converted to a variety of unsymmetrical biphenyl intermediates 23 as described in Scheme 1.

Scheme 6:

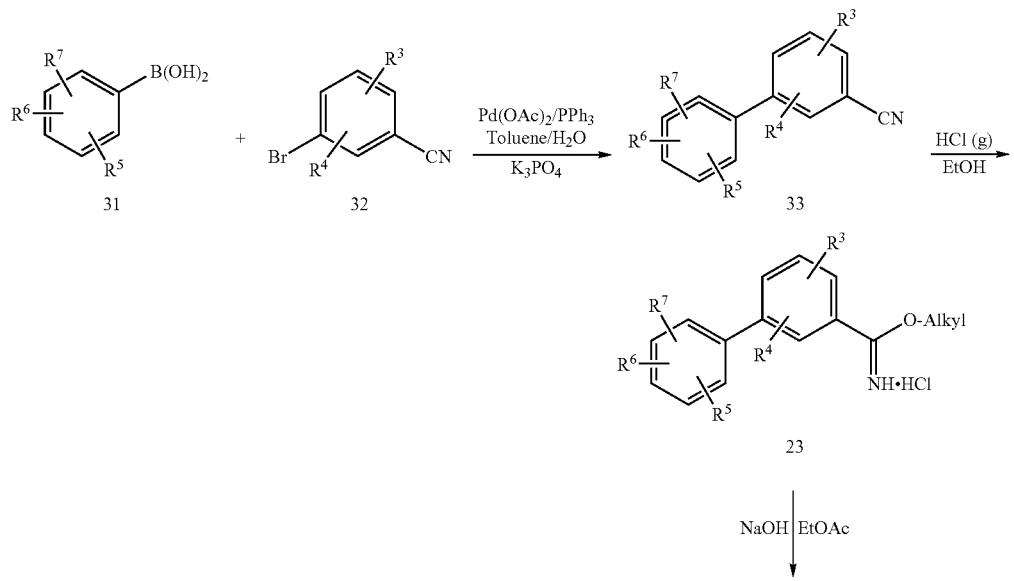

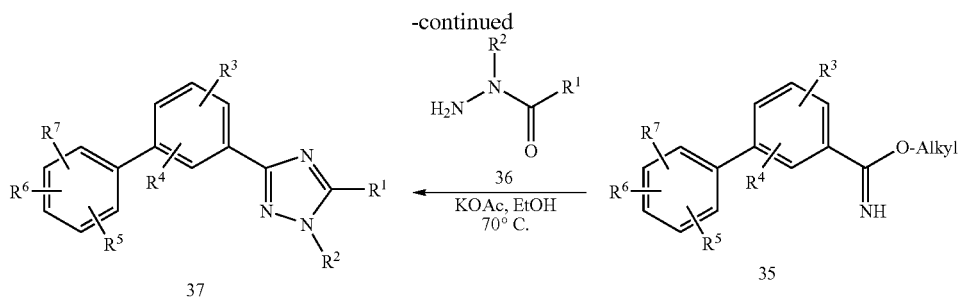

In accordance with Scheme 6, 31 and 32 can be converted to a biphenyl intermediate 33 by using, for example, a Suzuki-Miyaura coupling reaction with a palladium acetate/triphenyl phosphine catalyst system. The biphenyl intermediate 33 can be converted to imidate HCl salt 34 under standard Pinner conditions using, for example, a concentrated hydrochloric acid ethanolic solution. The imidate 34 can be converted to triazole 37 by free basing using a biphasic mixture such as EtOAc and NaOH to give ethyl imidate 35, followed by treatment with oxamic hydrazide 36, an alcoholic solvent such as ethanol and any one of many appropriate bases, including a metal acetate base such as potassium acetate, a tertiary amine base or a metal carbonate base, followed by heating.

Scheme 7:

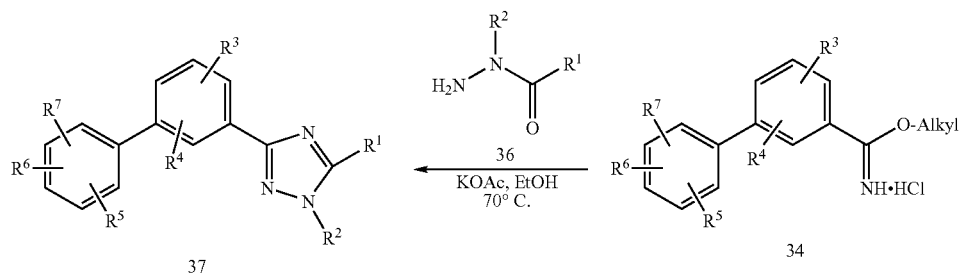

In a variation to Scheme 6, the imidate 34 is converted to triazole 37 by direct addition of oxamic hydrazide 36, an alcoholic solvent such as ethanol and any one of many appropriate bases, including a metal acetate base such as potassium acetate, a tertiary amine base, or a metal carbonate base, followed by heating.

Scheme 8:

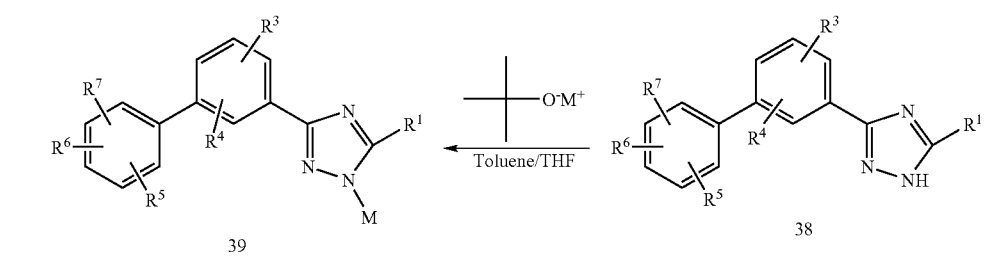

where M = K or Na

In accordance with Scheme 8, compounds of Formulas (I) or (II) wherein $R^2$ is H, 38, can be converted by deprotonation with a metal alkoxide base such as potassium tert-butoxide or sodium tert-butoxide in an appropriate solvent/co-solvent mixture to yield a salt 39.

EXAMPLE 1

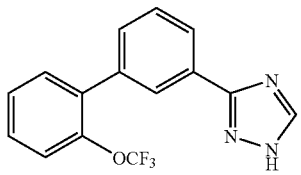

3-[3-(2-Trifluoromethoxyphenyl)-phenyl]-1,2,4-triazole

Step A: 2-Trifluoromethoxyphenylboronic acid

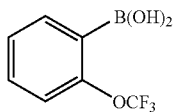

To a stirred solution of 2 g (9.5 mmol) of 1-bromo-2-trifluoromethoxy benzene in 28 Ml of tetrahydrofuran (THF) at −78° C., was carefully added a solution of 5.9 Ml of a 1.7 M solution of t-butyl lithium in hexanes (9.5 mmol). This reaction mixture was stirred at −78° C. for 45 min. To this reaction mixture at −78° C. was added 2.58 Ml (11.1 mmol) of tri-isopropyl borate and the mixture was slowly warmed to room temperature (RT) over a period of 16 h. The reaction mixture was diluted with water and made basic with 2N NaOH solution. The reaction mixture was washed with EtOAc. The aqueous fraction was acidified with 2N HCl solution and stirred for 1 h at RT. The reaction mixture was extracted with EtOAc and the organic fractions were washed with water, saturated NaCl solution (brine), dried over $Na_2SO_4$ and filtered. The filtrate was concentrated to give the title compound as a white solid. $^1HNMR$ ($CDCl_3$) (δ, ppm): 7.96 (dd, J=7.2, 1.6 Hz, 1 H), 7.53 (ddd, J=9.1, 7.3, 1.8 Hz, 1 H), 7.38 (td, J=7.3, 0.7 Hz, 1 H), 7.28 (d, J=8.2 Hz, 1H), 5.25 (br s, 2 H). MS (M+H): 206.9.

Step B: Ethyl-3-(2-Trifluoromethoxyphenyl)-benzoate

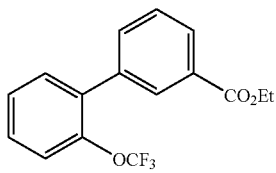

To a solution of 0.94 g (4.58 mmol) of ethyl-3-bromobenzoate in 14.5 Ml of toluene at RT was added 0.25 g (0.218 mmol) of tetrakis(triphenylphosphine) palladium(0), 0.94 g (4.58 mmol) of 2-trifluoromethoxyphenylboronic acid, 2.22 Ml (4.45 mmol) of 2M aqueous sodium carbonate solution and 7 Ml of ethanol. The reaction mixture was heated at reflux for 18 h. The reaction mixture was cooled and diluted with ethyl acetate and water. The organic fraction was separated and washed with saturated NaCl solution (brine), dried over $MgSO_4$, filtered and the filtrate was concentrated to an oil which was purified by chromatography (silica, 1%, 5%, 30% successively ethyl acetate:hexanes) to give the title compound. $^1H$ NMR ($CD_3OD$) (δ, ppm): 8.02 (s, 1H), 7.97 (dd, J=7.8, 1.2 Hz, 1H), 7.60 (dd, J=7.7, 1.3 Hz, 1H), 7.50-7.33 (m, 5H), 4.31 (q, 2H), 1.31 (t, 3H). Mass Spectrum (ESI) m/e (M+1): 311.2.

Step C: 3-(2-Trifluoromethoxyphenyl)-benzoic acid

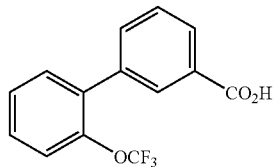

A solution of 0.3 g (4.19 mmol) of ethyl-3-(2-trifluoromethoxyphenyl)-benzoate and 8.3 Ml (8.3 mmol) of a 1N solution of NaOH in 12.5 Ml of methanol was stirred 18 h at RT. The reaction mixture was concentrated and the Ph was adjusted to Ph=2 with 1 N HCl solution. The mixture was extracted with ethyl acetate (EtOAc) and the organic fraction was dried over $MgSO_4$, filtered and the filtrate was concentrated to give the title compound as a white solid that was used without further purification.

Step D: 3-(2-Trifluoromethoxyphenyl)-benzamide

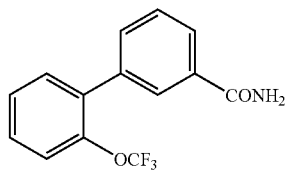

To a solution of 0.94 g (3.36 mmol) of 3-(2-trifluoromethoxyphenyl)-benzoic acid in 17 Ml of DMF was added 0.55 g (3.36 mmol) of carbonyldiimidazole (CDI) and the reaction was stirred at RT for 4 h. To the reaction mixture was added 2.6 g (33.6 mmol) of ammonium acetate and the reaction mixture was stirred over night at RT. The reaction mixture was partitioned between ethyl acetate and water and the organic fraction was washed with brine, dried over $MgSO_4$, filtered and the filtrate was concentrated. The residue was purified by chromatography (silica, 30%, 50% successively EtOAc:hexanes) to give the title compound. Mass Spectrum (ESI) m/e (M+1): 282.2.

Step E: 3-[3-(2-Trifluoromethoxyphenyl)-phenyl]-1,2,4-triazole

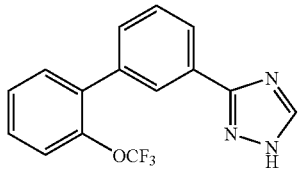

A solution of 0.137 g (0.48 mmol) of 3-(2-trifluoromethoxyphenyl)-benzamide in 1 Ml of N,N-dimethylformamide dimethyl acetal was heated at 120° C. for 2 h at which time the reaction was concentrated in vacuo. To this material in 2.3 Ml of acetic acid was added 0.028 g (0.55 mmol) of hydrazine hydrate and the reaction mixture was heated at 90° c. for 2 h. The reaction mixture was then concentrated and partitioned between EtOAc and saturated NaHCO$_3$ solution. The organic fraction was washed with brine, dried over MgSO$_4$, filtered and the filtrate was concentrated. The residue was purified by chromatography (silica, 30:1, 9:1, 3:1 successively CH$_2$Cl$_2$: acetone) to give the title compound. $^1$H NMR (CD$_3$OD) (δ,.ppm): 8.32 (s, 1H), 8.06 (s, 1H), 7.98 (m, 1H), 7.50 (m, 3H), 7.39 (m, 3H). Mass Spectrum (ESI) m/e (M+1): 306.1.

The following Examples 2-7 were prepared using procedures similar to that described in Example 1. The preparation of any intermediates that were not commercially available are described.

EXAMPLE 2

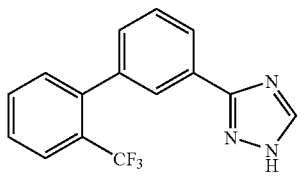

3-[3-(2-Trifluoromethyphenyl)-phenyl]-1,2,4-triazole

Mass Spectrum (ESI) m/e (M+1): 290.1.

EXAMPLE 3

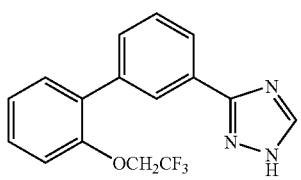

3-[3-(2-(2,2,2-Trifluoroethoxyphenyl)-phenyl]-1,2,4-triazole

Step A: 2-(2,2,2-Trifluoroethoxy)phenyl bromide

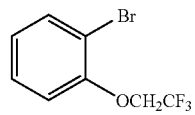

A solution of 0.35 g (2 mmol) of 2-bromophenol, 0.63 g (3 mmol) of 2,2,2-trifluoroethyliodide, 0.55 g (4 mmol) of potassium carbonate in 2 Ml of DMF was reacted at 150° C. in a microwave system (Personal Chemistry, Smithcreator) for 30 min. After cooling to RT, the reaction mixture was diluted with water and extracted with ethyl acetate. The organic fraction was dried over MgSO$_4$, filtered and the filtrate was concentrated. The residue was purified by chromatography (5%, 10% successively EtOAc:hexanes) to give the title compound.

Step B:
Ethyl-3-(2-(2,2,2-trifluoroethoxyphenyl)-benzoate

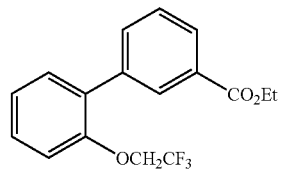

To a solution of 2.5 g (9.8 mmol) of 2-trifluoroethoxyphenyl bromide in 33 Ml of toluene at RT was added 0.57 g (0.49 mmol) of tetrakis(triphenyl-phosphine) palladium(0), 0.2 g (10.3 mmol) of 3-ethoxycarbonylphenylboronic acid, 5.9 Ml (11.8 mmol) of 2M aqueous sodium carbonate solution and 17 Ml of ethanol. The reaction mixture was heated at reflux for 18 h. The reaction mixture was cooled and diluted with ethyl acetate and water. The organic fraction was separated and washed with saturated NaCl solution (brine), dried over MgSO$_4$, filtered and the filtrate was concentrated to an oil which was purified by chromatography (silica, 1%, 5%, 30% successively ethyl acetate:hexanes) to give the title compound. Mass Spectrum (ESI) m/e (M+1): 325.1.

Step C: 3-[3-(2-(2,2,2-Trifluoroethoxyphenyl-phenyl]-1,2,4-triazole

The title compound can be prepared using procedures similar to that described in Example 1, Steps C-E.

EXAMPLE 4

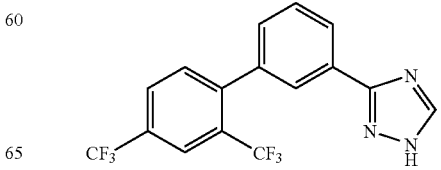

3-[3-((2,4-Bis-trifluoromethyl)-phenyl)-phenyl]-1,2,4-triazole

Mass Spectrum (ESI) m/e (M+1): 358.3.

EXAMPLE 5

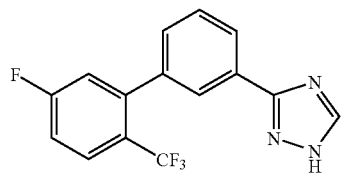

3-[3-((2-Trifluoromethyl-5-fluoro)-phenyl)-phenyl]-1,2,4-triazole

Mass Spectrum (ESI) m/e (M+1): 308.0.

EXAMPLE 6

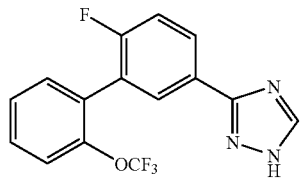

3-[3-((2-Trifluoromethoxy)phenyl)-(4-fluoro)-phenyl]-1,2,4-triazole

Mass Spectrum (ESI) m/e (M+1): 324.1.

EXAMPLE 7

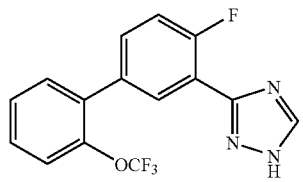

3-[3-((2-Trifluoromethoxy)-phenyl)-(6-fluoro)phenyl]-1,2,4-triazole

Mass Spectrum (ESI) m/e (M+1): 324.0.

EXAMPLE 8

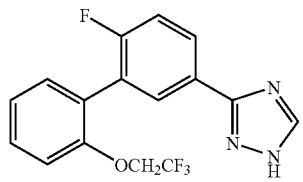

3-[3-((2-(2,2,2-Trifluoroethoxy)-phenyl)-(4-fluoro)phenyl]-1,2,4-triazole

Mass Spectrum (ESI) m/e (M+1): 338.0.

Step A:
Methyl-3-((2-hydroxy)phenyl)-4-fluorobenzoate

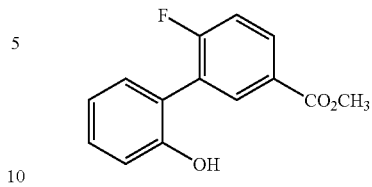

To a solution of 2 g (8.45 mmol) of methyl-3-bromo-4-fluorobenzoate in 28 Ml of toluene at RT was added 0.49 g (0.42 mmol) of tetrakis(triphenyl phosphine)palladium(0), 1.95 g (8.9 mmol) of 2-(4,4,5,5,-tetramethyl-1.3.2-dioxaborolan-2-yl)phenol, 5.1 Ml (10.15 mmol) of 2M aqueous sodium carbonate solution and 14 Ml of n-propanol. The reaction mixture was heated at reflux for 18 h. The reaction mixture was cooled and diluted with ethyl acetate and water. The organic fraction was separated and washed with saturated NaCl solution (brine), dried over $MgSO_4$, filtered and the filtrate was concentrated to an oil which was purified by chromatography (silica, 90:1, 30:1 successively $CH_2Cl_2$:acetone) to give the title compound. Mass Spectrum (ESI) m/e (M+1): 247.0.

Step B: Methyl-3-((2-(2,2,2-trifluoroethoxy)phenyl)-4-fluorobenzoate

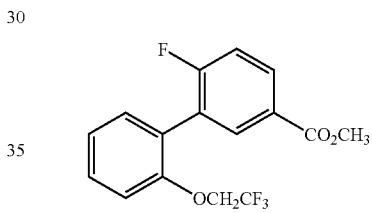

A mixture of 1.7 g (7.1 mmol) of methyl-3-((2-hydroxy)phenyl)-4-fluorobenzoate, 2.46 g (10.6 mmol) of 2,2,2,-trifluoroethyl trifluoromethanesulfonate and 3.45 g (10.6 mmol) of cesium carbonate in 35 Ml of DMF was stirred at 60° C. for 18 h. The cooled reaction mixture was partitioned between EtOAc and water. The aqueous layer was extracted with EtOAc and the combined organic fractions were washed with water, brine, dried over $MgSO_4$ and filtered. The filtrate was concentrated and purified by chromatography (silica, 5%, 30% successively EtOAc:hexanes) to give the title compound as a white solid. Mass Spectrum (ESI) m/e (M+1): 329.0.

Step C: 3-[3-((2-(2,2,2-Trifluoroethoxy)-phenyl)-(4-fluoro)phenyl]-1,2,4-triazole The title compound can be prepared using procedures similar to that described in Example 1, Steps C-E.

EXAMPLE 9

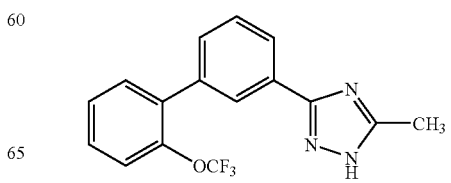

5-Methyl-3-[3-((2-trifluoromethoxy)phenyl)-phenyl]-1,2,4-triazole

Step A: 3-Bromophenylcarbonyl-(N-t-butoxycarbonyl)hydrazide

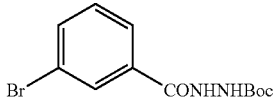

A solution of 1 g (4.97 mmol) of 3-bromobenzoic acid, 0.59 g (4.52 mmol) of t-butylcarbazate, 0.95 g (4.97 mmol) of EDC [1-(3-dimethylaminopropyl)-3-ethylcarbodiimide), 0.67 g (4.97 mmol) of hydroxybenzotriazole (HOBt) and 3.15 Ml (18.1 mmol) of diisopropylethylamine in 23 Ml of $CH_2Cl_2$ was stirred at RT for 18 h. The reaction mixture was diluted with $CH_2Cl_2$ and washed with 1N HCl solution, saturated $NaHCO_3$ solution and brine. The solution was dried over $MgSO_4$, filtered and the filtrate was concentrated. The residue was purified by chromatography (silica, 30:1, 9:1, 3:1 successively $CH_2Cl_2$:acetone) to give the title compound.

Mass Spectrum (ESI) m/e (M): 314.0, (M+2): 316.0

Step B: 3-((2-Trifluoromethoxy)phenyl)-phenylhydrazide

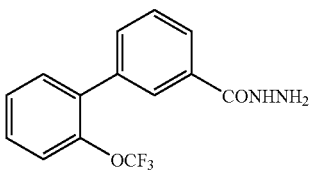

A solution of 0.22 g (1.07 mmol) of 2-trifluoromethoxyphenylboronic acid and 0.32 g (1.02 mmol) of 3-bromophenylcarbonyl-N-t-butoxycarbonylhydrazide in 5 Ml of toluene and 2.5 Ml of n-propanol was stirred for 30 min. To this reaction mixture was added 0.0007 g (0.003 mmol) of palladium acetate, 0.0024 g (0.009 mmol) of triphenylphosphine and 0.61 Ml (1.2 mmol) of a 2M aqueous sodium carbonate solution and the reaction mixture was heated at reflux for 18 h. The reaction mixture was cooled and diluted with EtOAc and water. The organic fraction was dried over $MgSO_4$, filtered and the filtrate was concentrated. The residue was purified by chromatography (silica, 30:1, 9:1 successively, $CH_2Cl_2$:acetone) to give the protected hydrazide which was then dissolved in a mixture of 2.1 Ml of TFA and 2.1 Ml of $CH_2Cl_2$. The reaction mixture was stirred for 2 h whereupon it was concentrated, dissolved in $CH_2Cl_2$ and washed with 1N NaOH solution. The organic fraction was dried over $MgSO_4$, filtered and the filtrate was concentrated to give the tile compound as a white solid. Mass Spectrum (ESI) m/e (M+1): 297.1.

Step C: 5-Methyl-3-[3-((2-trifluoromethoxy)phenyl)-phenyl]-1,2,4-triazole

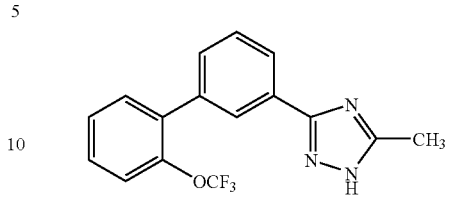

To a solution of 0.093 g (0.98 mmol) of acetamidine hydrochloride in 1.1 Ml of ethanol was added 0.22 Ml (0.98 mmol) of a 25% solution of sodium methoxide in methanol and the reaction mixture was stirred for 30 min. whereupon it was filtered. To the filtrate was added 0.19 g (0.66 mmol) of 3-((2-trifluoromethoxy)phenyl)-bromophenylhydrazide and the reaction mixture was stirred over night. The reaction mixture was concentrated and purified by chromatography (silica, 3%, 10%, 30% successively, methanol:$CH_2Cl_2$) to give a white solid. The white solid was heated (neat) to its melting temperature for 30 min. The reaction was cooled to RT, dissolved in $CH_2Cl_2$ and concentrated. The residue was purified by chromatography (silica, 3%, 10%, successively, methanol:$CH_2Cl_2$) to give the title compound as a white solid. $^1$H NMR ($CD_3OD$) (δ,.ppm): 8.00 (s, 1H), 7.93 (m, 1H), 7.49-7.34 (m, 6H), 2.41 (s, 3H). Mass Spectrum (ESI) m/e (M+1): 320.5.

The following Examples 10 to 18 were prepared according to the procedure described in Example 9, using the corresponding substituted amidine.

EXAMPLE 10

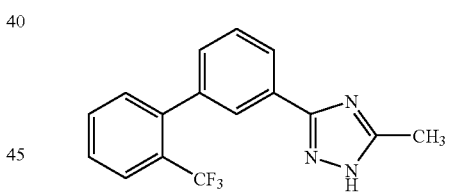

5-Methyl-3-[3-((2-trifluoromethyl)-phenyl)-phenyl]-1,2,4-triazole

Mass Spectrum (ESI) m/e (M+1): 304.0.

EXAMPLE 11

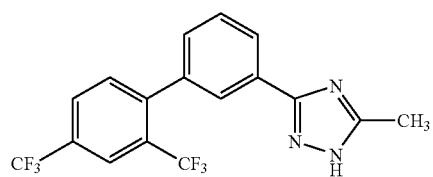

5-Methyl-3-[3-((2,4-bis(trifluoromethyl)-phenyl)-)-phenyl]-1,2,4-triazole

Mass Spectrum (ESI) m/e (M+1): 372.5.

EXAMPLE 12

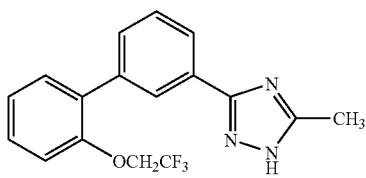

5-Methyl-3-[3-((2-(2,2,2-trifluoroethoxy)-phenyl)-phenyl]-1,2,4-triazole

Mass Spectrum (ESI) m/e (M+1): 334.1.

The title compound was prepared from the acid of ethyl-3-(2-trifluoroethoxyphenyl)-benzoate which was prepared in Example 3, Step B.

EXAMPLE 13

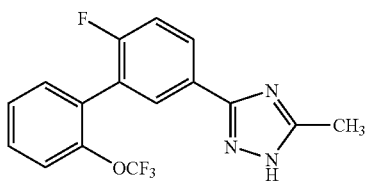

5-Methyl-3-[3-((2-trifluoromethoxy)phenyl)-(4-fluoro)-phenyl]-1,2,4-triazole

Mass Spectrum (ESI) m/e (M+1): 338.1.

EXAMPLE 14

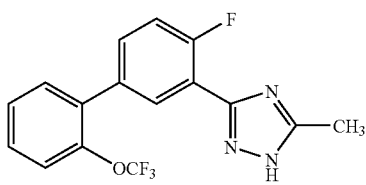

5-Methyl-3-[3-((2-trifluoromethoxy)phenyl)-(6-fluoro)-phenyl]-1,2,4-triazole

Mass Spectrum (ESI) m/e (M+1): 338.1.

EXAMPLE 15

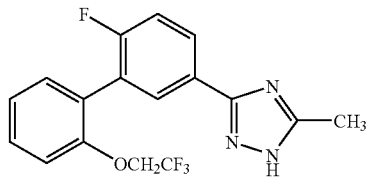

5-Methyl-3-[3-((2-(2,2,2-trifluoroethoxy)phenyl)-(4-fluoro)-phenyl]-1,2,4-triazole Mass Spectrum (ESI) m/e (M+1): 352.0.

The title compound was prepared from the acid of Methyl-3-(2-trifluoroethoxy-(4-fluoro)-phenyl)-benzoate which was prepared in Example 8, Step B.

EXAMPLE 16

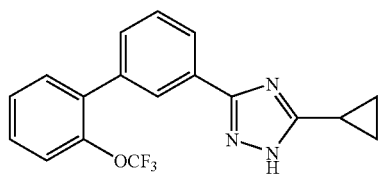

5-Cyclopropyl-3-[3-((2-trifluoromethoxy)-phenyl)-phenyl]-1,2,4-triazole

Mass Spectrum (ESI) m/e (M+1): 346.2.

EXAMPLE 17

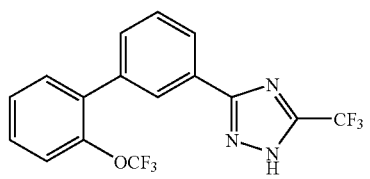

5-Trifluoromethyl-3-[3-((2-trifluoromethoxy)-phenyl)-phenyl]-1,2,4-triazole

Mass Spectrum (ESI) m/e (M+1): 374.1.

EXAMPLE 18

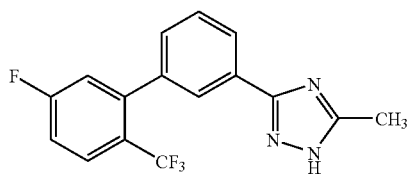

5-Methyl-3-[3-((2-trifluormethxy-5-fluoro)-phenyl)-phenyl]-1,2,4-triazole

Mass Spectrum (ESI) m/e (M+1): 321.9.

EXAMPLE 19

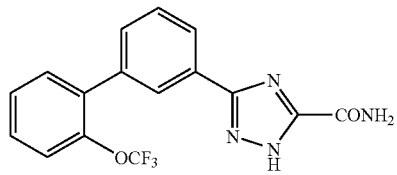

3-[3-((2-Trifluoromethoxy)-phenyl)-phenyl]-1,2,4-triazole-5-carboxamide

Step A: Ethyl-$N^1$-3-(2-trifluoromethoxy)-benzoyl-$N^2$-oxamidrazonate

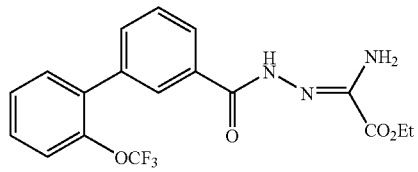

To a solution of 0.45 g (1.54 mmol) of 3-(2-trifluoromethoxyphenyl)-bromophenylhydrazide (Example 9, Step B) in 20 Ml of $CH_2Cl_2$ was added 0.54 g (2.3 mmol) of carbethoxy-S-methylthioformimidium tetrafluoroborate and 0.43 Ml (3.08 mmol) of triethylamine and the reaction was stirred at refluxing temperatures for 4 hr. The reaction mixture was cooled to RT, washed with water, dried over $Na_2SO_4$, filtered and the filtrate was concentrated to a solid. Two Ml of $CH_2Cl_2$ was added and the resulting solid product was recovered by filtration. Mass Spectrum (ESI) m/e (M+1): 396.1.

Step B: 5-Ethyl-3-[3-((2-trifluoromethoxy)-phenyl)-phenyl]-1,2,4-triazole-5-carboxylate The solid Ethyl-$N^1$-3-(2-trifluoromethoxy)-benzoyl-$N^2$-oxamidrazonate (0.25 g, 0.616 mmol) was heated in an oil bath above its melting point for 20 min. After cooling to RT, the residue was dissolved in $CH_2Cl_2$ and concentrated to give a yellow solid. It was purified by chromatography (silica, 10%, 30%, 50% successively, EtOAc:hexanes) to give a white solid. Mass Spectrum (ESI) m/e (M+1): 378.1.

Step C: 3-[3-((2-Trifluoromethoxy)-phenyl)-phenyl]-1,2,4-triazole-5-carboxamide

A solution of 0.13 g (0.34 mmol) of 5-ethyl-3-[3-((2-trifluoromethoxy)phenyl)-phenyl]-1,2,4-triazole-5-carboxylate in 2 Ml of methanol in a tube was saturated with ammonia. The tube was sealed and the reaction mixture was heated at 60° C. overnight. The reaction mixture was then concentrated and the residue was purified by chromatography (silica, 3%, 10%, 20% successively methanol:$CH_2Cl_2$) to give the title compound. $^1$H NMR ($CD_3OD$) (δ,.ppm): 8.10 (s, 1H), 8.02 (m, 1H), 7.54-7.36 (m, 6H). Mass Spectrum (ESI) m/e (M+1): 349.2.

EXAMPLE 20

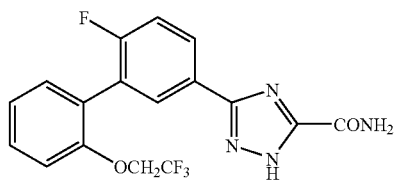

3-[3-((2-(2,2,2-Trifluoroethoxy)-phenyl)-4-fluorophenyl]-1,2,4-triazole-5-carboxamide Step A: 3-((2-(2,2,2-Trifluoroethoxy)-phenyl)-4-fluorobenzoic acid

To a solution of 0.75 g (2.29 mol) of Methyl 1-3-((2-trifluoroethoxy)phenyl)-4-fluorobenzoate (Example 8, Step B) in 11.5 Ml of a 3:1 mixture of THF:water was added 0.164 g (6.86 mmol) of LiOH and the reaction mixture was stirred at RT for 18 hr. The reaction mixture was concentrated and the Ph was adjusted to Ph=2 with 1N HCl solution. The mixture was extracted with EtOAc and the combine organic fractions were washed with brine, dried over $MgSO_4$, filtered and the filtrate was concentrated to give the title compound which was used without further purification.

Step B: 3-[3-((2-(2,2,2-Trifluoroethoxy)-phenyl)-4-fluorophenyl]-1,2,4-triazole-5-carboxamide The title compound was prepared from 3-((2-trifluoroethoxy)phenyl)-4-fluorobenzoic acid according to procedures described in Example 9 Steps A&B and Example 19. $^1$H NMR ($CD_3OD$) (δ, ppm): 8.02 (m, 2H), 7.99 (m, 1H), 7.39 (m, 1H), 7.30 (m, 1H), 7.16 (m, 2H), 4.45 (q, J=8.5 Hz, 2H). Mass Spectrum (ESI) m/e (M+1): 381.0.

The following Examples 21-26 were prepared according to procedures described in Examples 19 and 20.

EXAMPLE 21

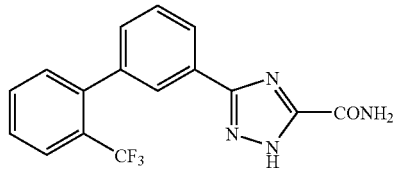

3-[3-((2-Trifluoromethyl)-phenyl)-phenyl]-1,2,4-triazole-5-carboxamide

Mass Spectrum (ESI) m/e (M+1): 333.1.

EXAMPLE 22

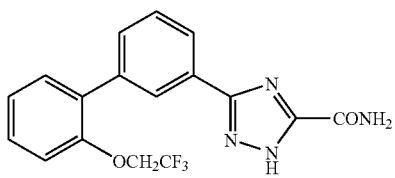

3-[3-((2-(2,2,2-Trifluoroethoxy)-phenyl)-phenyl]-1,2,4-triazole-5-carboxamide

Mass Spectrum (ESI) m/e (M+1): 363.1.

EXAMPLE 23

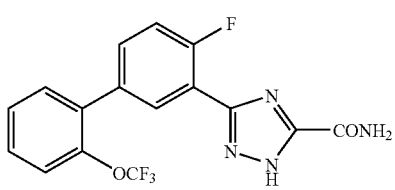

3-[3-((2-Trifluoromethoxy)-phenyl)-(6-fluoro)-phenyl]-1,2,4-triazole-5-carboxamide Mass Spectrum (ESI) m/e (M+1): 367.0.

EXAMPLE 24

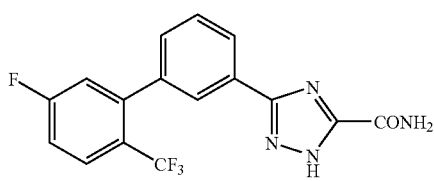

3-[3-((2-Trifluoromethyl-5-fluoro)-phenyl)-phenyl]-1,2,4-triazole-5-carboxamide

Mass Spectrum (ESI) m/e (M+1): 351.0.

EXAMPLE 25

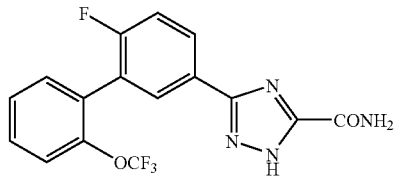

3-[3-((2-Trifluoromethoxy)-phenyl)-(4-fluoro)-phenyl]-1,2,4-triazole-5-carboxamide Mass Spectrum (ESI) m/e (M+1): 367.0.

Step A: Preparation of 4-fluoro-3-(2-trifluoromethoxyphenyl)benzonitrile 3-bromo-4-fluorobenzonitrile (1.0 equivalent), 2-(trifluoromethoxy)benzeneboronic acid (1.25 equivalent), palladium acetate (0.005 equivalent) and triphenylphosphine (0.01 equivalent) were sequentially charged to a multi-necked flask. After purging the flask with nitrogen, toluene (5 mL/gram of 3-bromo-4-fluorobenzonitrile) was added and the resulting slurry was stirred while bubbling nitrogen subsurface for about 20 minutes. In a separate flask, an aqueous potassium phosphate solution was prepared by dissolving solid potassium phosphate (2.0 equivalents) into water (2 mL/gram of potassium phosphate). The resulting solution was de-oxygenated by bubbling nitrogen subsurface while stirring for about 30 minutes. The aqueous potassium phosphate solution was added to the toluene slurry and the reaction mixture was warmed to 60-65° C. by heating with steam. The progress of the reaction was monitored by HPLC and the reaction temperature was held between 63-69° C. When 3-bromo-4-fluorobenzonitrile was consumed, heating was discontinued and the reaction mixture was cooled to RT using an ice bath. The aqueous layer was siphoned from the vessel and Ecosorb C-941 (0.5 gram/grams of 3-bromo-4-fluorobenzonitrile, commercially available from Graver Technologies, Glasgow, Del.) was added to the reaction vessel. The resulting black slurry was stirred at RT for 15 hours. The carbon was removed by filtering the slurry through a pad of solka flok on a filter pot. The filter cake was washed with toluene (4 mL/gram of 3-bromo-4-fluorobenzonitrile). The combined filtrates were batch concentrated (40-50° C.) to provide the biaryl nitrile product as a thick, light-orange oil (94.0% yield).

Step B: Preparation of

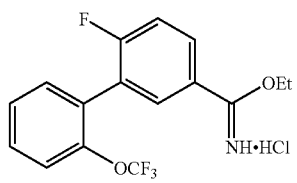

Absolute ethanol (1.8 mL/gram of biaryl nitrile) was charged to a round bottom flask. The stirred ethanol was chilled with an ice/acetone bath and gaseous hydrogen chloride was bubbled subsurface while the internal temperature was maintained less than 20° C. Addition of HCl was monitored by proton titration using a Metrohm 808 Titrando (commercially available from Metrohm Ltd.) to determine HCl concentration of the ethanol solution. The addition was stopped after the concentration of HCl reached 38% (7.5 equivalents). The biaryl nitrile from step A (1.0 equivalent) was added as a neat oil to the chilled ethanolic HCl solution and the reaction solution was allowed to warm to RT while being stirred overnight (>15 h). The reaction was deemed complete when assay by HPLC showed no presence of the starting biaryl nitrile. The resulting reaction was then diluted with toluene (8 mL/gram of biaryl nitrile). To induce crystallization, the batch was solvent switched to toluene by co-distillation with ethanol (<35° C. internal temperature) which azeotropically removed ethanol. This process was carried out until the ethanol content in the mother liquor was less than 1 mol % relative to toluene. This endpoint was determined by proton NMR in CDCl$_3$ of the mother liquor. The solids were isolated by filtration, washed with toluene (2.3 mL/gram of biaryl nitrile). The white crystalline HCl salt of the ethyl imidate product was dried under a stream of nitrogen.

Step C: Preparation of

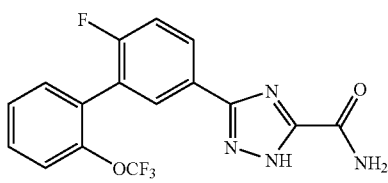

The imidate HCl salt from Step B (1.0 equivalent) and EtOAc (4 mL/gram of imidate HCl salt) were added to a flask, followed by stirring to give a heterogeneous slurry. This slurry was cooled to 10° C. followed by the slow addition of a solution of 5.0 N NaOH (3.3 equivalents). The rate of addition of the NaOH solution was periodically adjusted to maintain the reaction temperature below 15° C. Once the addition of NaOH was complete, the biphasic reaction mixture was allowed to warm to ambient temperature at which point all of the solids had dissolved (ca. 30 min). Stirring was stopped and the two layers were allowed to separate. The bottom aqueous layer was removed and discarded. To the flask containing the organic layer was added water (2 mL/gram of HCl imidate salt) and the resulting biphasic mixture was stirred for 5 minutes. The layers were allowed to separate and the bottom aqueous layer was removed and discarded. This was followed by the addition of a 10% NaCl aqueous solution (2 mL/gram of HCl imidate salt) to the flask. The resulting two layers were stirred for 5 minutes, and the bottom aqueous layer was removed and discarded. The top organic layer was transferred to a round bottom flask that was connected to a batch concentrator. A solvent switch from EtOAc to EtOH was then performed by removing the EtOAc by co-distillation with EtOH. Once the solvent switch was complete (<3% EtOAc by $^1$H NMR, imidate concentration approximately 185 mg/mL), the ethanolic solution containing the free base imidate was transferred to a new flask.

Oxamic hydrazide (1.1 equivalents) and potassium acetate (5.0 equivalents) were added to the ethanol solution containing the imidate from above. The resulting heterogeneous mixture was then heated to between 60-70° C. using a steam batch along with vigorous stirring. The reaction was monitored by HPLC analysis for conversion of the imidate to the desired triazole product. Once the reaction was complete, it was cooled to ambient temperature followed by the slow addition of water (4 mL/gram of imidate HCl salt) to crystallize the desired product from the reaction. The desired product was then collected by vacuum filtration as an off-white solid (85% yield).

Step D: Preparation of

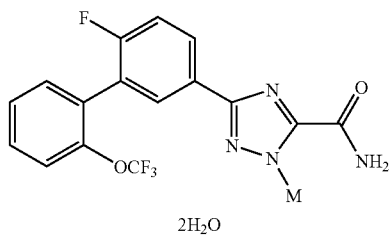

where M = K or Na

The triazole product of Step C (1.0 equivalents) was added to a reaction vessel, followed by the addition of toluene (5.3 mL/gram of triazole) and THF (1.7 mL/gram of triazole). The resulting heterogeneous mixture was stirred at ambient temperature. To this slurry was added a solution of potassium tert-butoxide (1.1 equivalents). The rate of addition of the base was periodically adjusted to maintain the reaction temperature below 35° C. As the addition proceeded, the reaction mixture became less heterogeneous. Once the addition of the base was complete, the now homogeneous light yellow solution was allowed to stir at ambient temperature for 30 min. At this point, water (2.5 equivalents) was slowly added (ca. 10 min) to the batch with no noticeable exotherm. After about 15 min, the reaction became increasingly cloudy and the batch temperature slowly began to rise. Approximately 20 min after addition of water, solids began to form indicating the crystallization had begun. After about 30 min, the batch temperature had reached its maximum (24.9° C.). The heterogeneous batch was allowed to stir for an additional 30 minutes. The batch was filtered onto a filter pot using the mother liquor to obtain any residual solids in the reaction vessel. The wet cake was washed with fresh toluene (4 mL/gram of triazole). The batch was transferred to a vacuum oven and dried at 45° C. and 100 torr for 24 hours to provide the potassium salt dihydrate product as a white solid (95% yield).

EXAMPLE 26

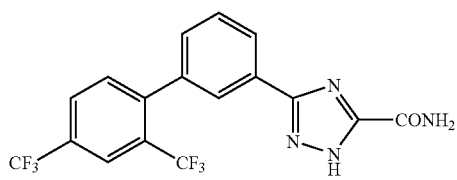

3-[3-((2,4-bis(trifluoromethyl)-phenyl)-phenyl]-1,2,4-triazole-5-carboxamide

Mass Spectrum (ESI) m/e (M+1): 401.0.

EXAMPLE 26 AND 26'

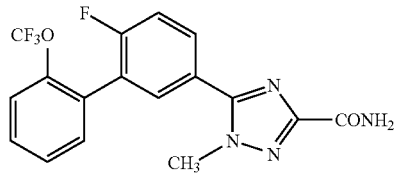

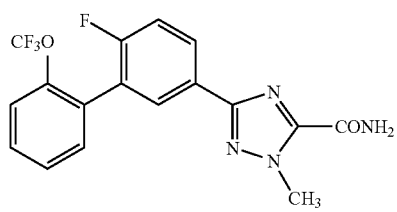

2-Methyl-3-[3-((2-trifluoromethoxy)-phenyl)-(4-fluoro)-phenyl]-1,2,4-triazole-5-carboxamide (26) and 1-Methyl-3-[3-((2-trifluoromethoxy)-phenyl)-(4-fluoro)-phenyl]-1,24-triazole-5-carboxamide (26')

To a solution of 0.12 g (0.328 mmol) of 3-[3-((2-trifluoromethoxy)phenyl)-(4-fluoro)-phenyl]-1,2,4-triazole-5-carboxamide (Example 25) in 1.5 Ml of methanol was added 0.1 Ml (0.46 mmol) of a solution of NaOCH₃ (25% in methanol) and 0.02 Ml of methyl iodide. The tube was sealed and heated overnight at 100° C. The reaction mixture was concentrated and the residue was purified by chromatography (silica, 30:1, 9:1, 1% successively methanol:CH₂Cl₂) to give the title compounds.
(26) ¹H NMR (CD₃OD) (δ,.ppm): 8.09 (m, 1H), 8.00 (dd, J=7.1, 2.3 Hz, 1H), 7.50-7.36 (m, 4H), 7.23 (t, J=9.2 Hz, 1H), 4.18 (s, 3H). Mass Spectrum (ESI) m/e (M+1): 381.0
(26' ¹H NMR (CD₃OD) (δ,.ppm): 7.84 (m, 1H), 7.77 dd, J=6.6, 2.3 Hz, 1H), 7.52-7.44 (m, 5H), 4.00 (s, 3H). Mass Spectrum (ESI) m/e (M+1): 381.0.
The following Examples 27/27' and 28/28' were prepared according to the procedure described in Example 26 and 26'.

EXAMPLE 27 AND 27'

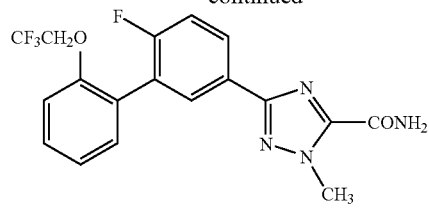

-continued

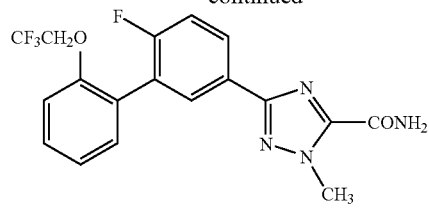

2-Methyl-3-[3-((2-(2,2,2-trifluoroethoxy)phenyl)-4-fluorophenyl]-1,2,4-triazole-5-carboxamide (27) and 1-Methyl-3-[3-((2-(2,2,2-trifluoroethoxy)phenyl)-4-fluorophenyl]-1,2,4-triazole-5-carboxamide (27')

(27) Mass Spectrum (ESI) m/e (M+1): 395.2.
(27') Mass Spectrum (ESI) m/e (M+1): 395.2.

EXAMPLE 28 AND 28'

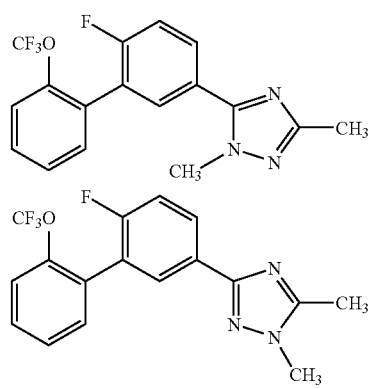

2,5-dimethyl-3-[3-((2-trifluoromethoxy)-phenyl)-4-fluorophenyl]-1,2,4-triazole (28) and 1,5-dimethyl-3-[3-((2-trifluoromethoxy)-phenyl)-4-fluorophenyl]-1,2,4-triazole-5-carboxamide (28')

(28) Mass Spectrum (ESI) m/e (M+1): 334.2.
(28') Mass Spectrum (ESI) m/e (M+1): 334.2.

EXAMPLE 29

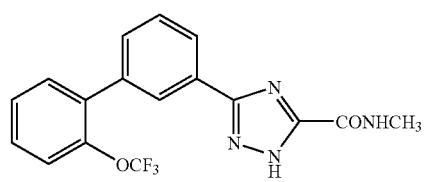

N-Methyl-3-[3-((2-trifluoromethoxy)-phenyl)-phenyl]-1,2,4-triazole-5-carboxamide To a solution of 0.083 g (0.24 mmol) of 3-[3-((2-trifluoromethoxy)-phenyl)-phenyl]-1,2,4-triazole-5-carboxylic acid (made from 5-ethyl-3-[3-((2-trifluoromethoxy)phenyl)-phenyl]-1,2,4-triazole-5-carboxylate Example 19 according to procedures described in Example 20) in 1.2 Ml of DMF at RT was added 0.038 g (0.24 mmol) of carbonyldiimidazole (CDI) and the reaction mixture was stirred for 3 hr. To the reaction mixture was added 1.2 Ml (2.4 mmol) of a 2M solution of methylamine in THF and the reaction mixture was stirred overnight at RT. The reaction mixture was concentrated and partitioned between EtOAc and water. The aqueous fraction was extracted with EtOAc and the combined organic fractions were washed with water and brine, dried over MgSO$_4$, filtered and the filtrate was concentrated. The residue was purified by chromatography (silica, 30%, 50% successively EtOAc:hexanes) to give the title compound as a foamy white solid. Mass Spectrum (ESI) m/e Mass Spectrum (ESI) m/e (M+1): 363.0.

The following Examples 30 and 31 were prepared using the procedure described in Example 29.

EXAMPLE 30

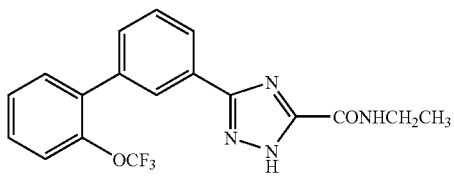

N-Ethyl-3-[3-((2-trifluoromethoxy)-phenyl)-phenyl]-1,2,4-triazole-5-carboxamide

Mass Spectrum (ESI) m/e (M+1): 377.2.

EXAMPLE 31

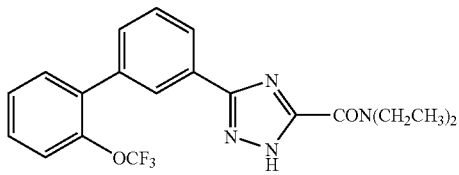

N,N-Diethyl-3-[3-((2-trifluoromethoxy)-phenyl)-phenyl]-1,2,4-triazole-5-carboxamide Mass Spectrum (ESI) m/e (M+1): 405.0.

EXAMPLE 32

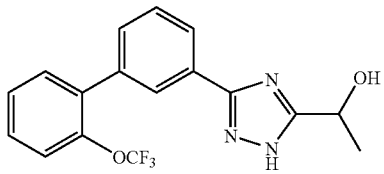

5-(1-Hydroxy-ethyl)-3-[3-((2-trifluoromethoxy)-phenyl)-phenyl]-1,2,4-triazole

To a solution of 0.007 Ml (0.133 mmol) of a 2M solution of LiBH$_4$ in THF at RT was added a solution 0.18 Ml (0.53 mmol) of a 3M solution of MeMgCl in THF. After stirring, the reaction mixture was cooled to −20° C. and to it was added a solution of 0.1 g (0.265 mol) of 5-ethyl-3-[3-((2-trifluoromethoxy)-phenyl)-phenyl]-1,2,4-triazole-5-carboxylate (Example 19) in 1 Ml of THF and the reaction mixture was stirred at −20° C. for 24 hr. The reaction mixture was poured into cold 1N HCl solution. The aqueous fraction was extracted with diethyl ether and the combined organic fractions were washed with brine, dried over MgSO$_4$, filtered and the filtrate was concentrated. The residue was purified by chromatography (silica, 9:1, CH$_2$Cl$_2$, acetone) to give the title compound. Mass Spectrum (ESI) m/e (M+1): 350.1.

EXAMPLE 33

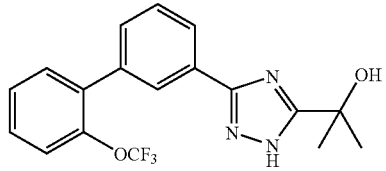

5-(1-Hydroxy-1-methyl-ethyl)-3-[3-((2-trifluoromethoxy)-phenyl)-phenyl]-1,2,4-triazole The title compound is a by-product of Example 32. Mass Spectrum (ESI) m/e (M+1): 364.1.

EXAMPLE 34

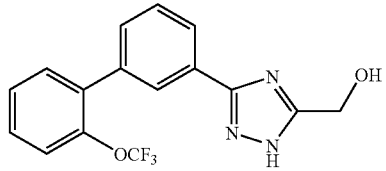

5-Hydroxymethyl-3-[3-((2-trifluoromethoxy)-phenyl)-phenyl]-1,2,4-triazole

The title compound is a by-product of Example 32. Mass Spectrum (ESI) m/e (M+1): 336.1.

EXAMPLE 35

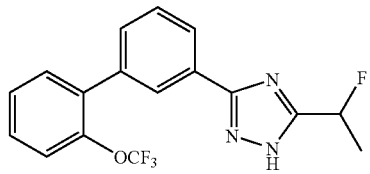

5-(1-Fluoro-ethyl)-3-[3-((2-trifluoromethoxy)-phenyl)-phenyl]-1,2,4-triazole To a solution of 0.13 g (0.37 mmol) of 5-(2-hydroxy)-ethyl-3-[3-((2-trifluoromethoxy)phenyl)-phenyl]-1,2,4-triazole in 2 Ml of $CH_2Cl_2$ at −78° C. was added 0.06 Ml of (diethylamino)sulfurtrifluoride (DAST) and the reaction was stirred at −78° C. for 1 hr. The reaction was quenched with a saturated solution of $NaHCO_3$. The organic fraction was washed with brine, dried over $MgSO_4$, filtered and the filtrate was concentrated. The residue was purified by chromatography (silica, 9:1 $CH_2Cl_2$:acetone) to give the title compound. Mass Spectrum (ESI) m/e (M+1): 352.0.

EXAMPLE 36

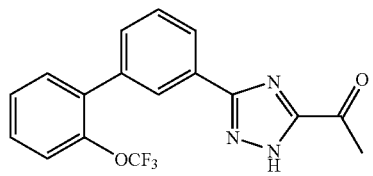

5-(Acetyl)-3-[3-((2-trifluoromethoxy)-phenyl)-phenyl]-1,2,4-triazole

To a suspension of 0.155 g (1.59 mmol) of N,O-dimethylhydroxylamine hydrochloride in 1.6 Ml of benzene at 5° C. was added 0.8 Ml (1.59 mmol) of a 2M solution of trimethylaluminum in toluene. The reaction mixture was warmed to RT and stirred for 1 hr. This solution was then added dropwise to a solution of 0.3 g (0.79 mmol) of 5-ethyl-3-[3-((2-trifluoromethoxy)phenyl)-phenyl]-1,2,4-triazole-5-carboxylate in 8 Ml of benzene and the reaction mixture was heated at reflux for 18 hr. The reaction mixture was cooled to RT and quenched with a 5% solution of HCl. The aqueous fraction was extracted with EtOAc and the combined organic fractions were dried over $MgSO_4$, filtered and the filtrate was concentrated. The residue was purified by chromatography (silica 10% methanol:$CH_2Cl_2$) to give the intermediate amide.

To a solution of 0.19 g (0.49 mmol) of the amide in 2.5 Ml of THF at 0° C. was added 0.41 Ml (1.22 mmol) of a 3M solution of methylmagnesium chloride in THF and the reaction was stirred at 0° C. for 1 hr, warmed to RT and stirred for 18 hr. The reaction mixture was partitioned between EtOAc and saturated $NH_4Cl$ solution. The organic fraction was washed with saturated $NaHCO_3$ solution, and brine. It was then dried over $MgSO_4$, filtered and the filtrate was concentrated. The residue solid was triturated with $CH_2Cl_2$ and the title compound was isolated as a solid by filtration. Mass Spectrum (ESI) (M+1): 348.1.

EXAMPLE 37

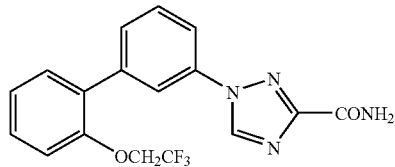

1-[3-((2-(2,2,2-Trifluoroethoxy)-phenyl)-phenyl]-1,2,4-triazole-3-carboxamide Step A: 3-((2-(2,2,2-Trifluoroethoxy)-phenyl)-aniline

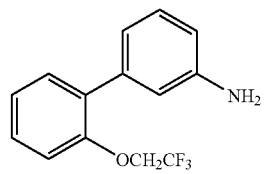

To a solution of 1.0 g (3.93 mmol) of 2-trifluoroethoxyphenyl bromide (Example 3, Step A) in 39 Ml of toluene was added 0.136 g (0.118 mmol) of tetrakis(triphenylphosphine)palladium(0), 0.56 g (4.31 mol) of 3-aminophenylboronic acid, 47 Ml (94.1 mmol) of a 2M solution of sodium carbonate and 8 Ml of ethanol and the reaction mixture was heated at 90° C. for 22 hr. The reaction mixture was cooled to RT, and partitioned between water and EtOAc. The aqueous fraction was extracted with EtOAc and the combined organic fractions were washed with water and brine and dried over $Na_2SO_4$, filtered and the filtrate was concentrated. The residue was purified by chromatography (silica, 4:1 hexanes:EtOAc) to give the title compound. Mass Spectrum (ESI) m/e M+1 268.1.

Step B: Methyl-1-[3-((2-(2,2,2-Trifluoroethoxy)-phenyl)-phenyl]-1,2,4-triazole-3-carboxylate

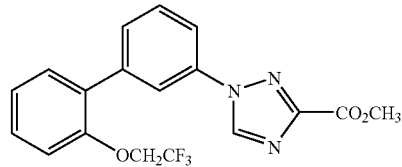

To a solution of 0.923 g (3.45 mmol) of 3-((2-trifluoroethoxy)-phenyl)analine in 6 Ml of a 1N solution of HCl at 0° C. was added 0.238 g (3.45 mmol) of sodium nitrite and 1 Ml of water and the reaction mixture was stirred for 20 min. to give the diazonium salt solution.

To a solution of 0.27 g (2.76 mmol) of methylisocyanoacetate in 15 Ml of methanol and 2 Ml of water at 0° C. was added 1.8 g (22.08 mmol) of sodium acetate. To this reaction mixture was added dropwise the diazonium salt solution and the reaction mixture was stirred at 0° C. for 1 h. The reaction mixture was then diluted with methanol and concentrated. The residue was diluted with EtOAc and 0.5N HCl solution. The aqueous layer was extracted with EtOAc and the combined organic fractions were washed with 5% $NaHCO_3$ solution, brine, dried over $Na_2SO_4$, filtered and the filtrate was concentrated. The residue was purified by chromatography (silica, 1:1 EtOAc:hexanes) to give the title compound. Mass Spectrum (ESI) m/e M+1 378.1.

Step C: 1-[3-((2-(2,2,2-Trifluoroethoxy)-phenyl)-phenyl]-1,2,4-triazole-3-carboxylic acid

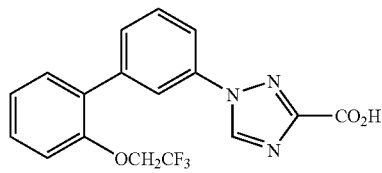

A solution of 0.29 g (0.769 mmol) of methyl-1-[3-((2-trifluoroethoxy)-phenyl)-phenyl]-1,2,4-triazole-3-carboxylate and 2.2 Ml (2.2 mmol) of a 1M solution of NaOH in water was stirred for 18 hr at RT. The reaction mixture was concentrated. The residue was diluted with water and the Ph was adjusted to 2-4 with 1N HCl solution. The mixture was extracted with EtOAc and the combined organic fractions were washed with brine, dried over $Na_2SO_4$, filtered and the filtrate was concentrated to give the title compound. Mass Spectrum (ESI) m/e M+1 363.9.

Step D: 1-[3-((2-(2,2,2-Trifluoroethoxy)-phenyl)-phenyl]-1,2,4-triazole-3-carboxamide To a solution of 0.225 g (0.619 mmol) of 1-[3-((2-trifluoroethoxy)phenyl)-phenyl]-1,2,4-triazole-3-carboxylic acid in 3.1 Ml of DMF was added 0.1 g (0.19 mmol) of CDI and the reaction mixture was stirred at RT for 4 hr. To the reaction mixture was added 0.477 g (6.19 mmol) of ammonium acetate and the reaction mixture was stirred for 19 hr. The reaction mixture was diluted with water and EtOAc and the aqueous layer was extracted with EtOAc. The combined organic fractions were washed with brine, dried over $Na_2SO_4$, filtered and the filtrate was concentrated. The residue was purified by chromatography (silica, 1:1 EtOAc:hexanes, 1% methanol:$CH_2Cl_2$, 10% methanol:$CH_2Cl_2$) to give the title compound. Mass Spectrum (ESI) m/e M+1 363.1.

EXAMPLE 38

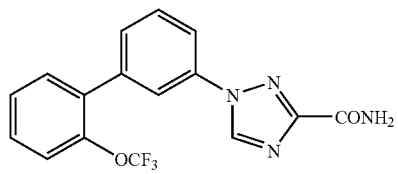

1-[3-((2-Trifluoromethoxy)-phenyl)-phenyl]-1,2,4-triazole-3-carboxamide

Step A:
1-N-t-butoxycarbonylamino-3-bromobenzene

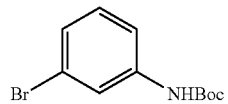

A solution of 10 g (58.13 mmol) of 3-bromoaniline and 15.2 g (69.75 mmol) of $Boc_2O$ in 300 Ml of toluene was heated overnight at 70° C. The reaction mixture was concentrated and diluted with EtOAc and 0.5N HCl solution. The organic fraction was washed with 0.5N HCl solution and brine. It was dried over $Na_2SO_4$, filtered and the filtrate was concentrated. The residue was purified by chromatography (hexanes, 9:1 hexanes:EtOAc successively) to give the title compound.

Step B: 1-N-t-butoxycarbonyl-3-((2-Trifluoromethoxy)-phenyl)analine

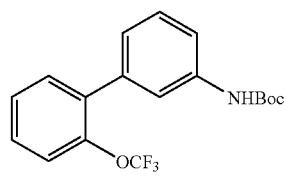

1-N-t-Butoxycarbonylamino-3-bromobenzene was coupled with 2-trifluoromethoxyphenylboronic acid according to procedures described in Example 37, Step A.

Step C: 3-((2-Trifluoromethoxy)-phenyl)aniline

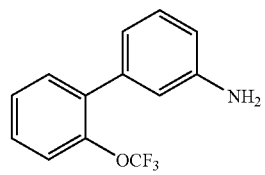

A solution of 0.977 g (2.77 mmol) of 1-N-t-butoxycarbonyl-3-((2-Trifluoromethoxy)-phenyl)analine in 7 Ml of TFA and 7 Ml of $CH_2Cl_2$ was stirred at RT for 1 hr. The reaction mixture was concentrated and the residue was diluted with 1N NaOH solution and EtOAc. The organic fraction was washed with 1N NaOH solution and brine, dried over $Na_2SO_4$ filtered and the filtrate was concentrated to give the title compound. Mass Spectrum (ESI) m/e M+1 254.1.

Step D: 1-[3-((2-Trifluoromethoxy)phenyl)-phenyl]-1,2,4-triazole-3-carboxamide

The title compound was prepared from 3-((2-Trifluoromethoxy)phenyl)aniline according to procedures described in Example 37. Mass Spectrum (ESI) m/e M+1 349.1.

The following Examples 39-40 were prepared according to the procedures described in Examples 37 or 38.

EXAMPLE 39

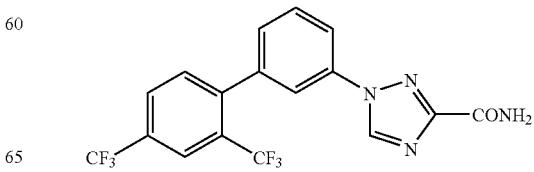

1-[3-((2,4-bis-trifluoromethyl)phenyl)-phenyl]-1,2,4-triazole-3-carboxamide

Mass Spectrum (ESI) m/e M+1 401.1.

EXAMPLE 40

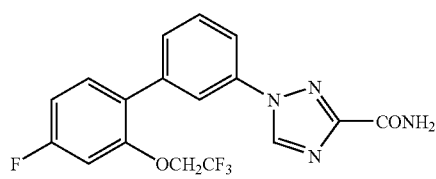

1-[3-((2-(2,2,2-Trifluoroethoxy-4-fluoro)phenyl)-phenyl]-1,2,4-triazole-3-carboxamide Mass Spectrum (ESI) m/e M+1 381.2.

The following Examples 41 to 44 were prepared according to procedures described in Example 29.

EXAMPLE 41

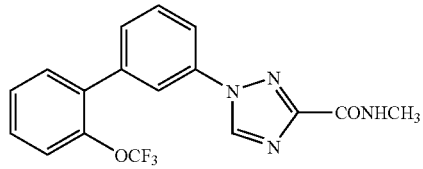

N-Methyl-1-[3-((2-trifluoromethoxy)phenyl)-phenyl]-1,2,4-triazole-3-carboxamide

Mass Spectrum (ESI) m/e M+1 363.1.

EXAMPLE 42

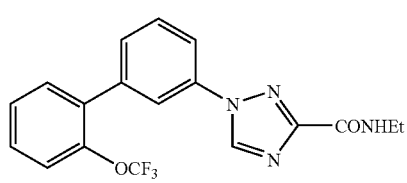

N-Ethyl-1-[3-((2-trifluoromethoxy)phenyl)-phenyl]-1,2,4-triazole-3-carboxamide

Mass Spectrum (ESI) m/e M+1 377.1.

EXAMPLE 43

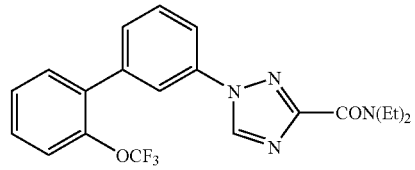

N,N-Diethyl-1-[3-((2-trifluoromethoxy)phenyl)-phenyl]-1,24-triazole-3-carboxamide Mass Spectrum (ESI) m/e M+1 405.2.

EXAMPLE 44

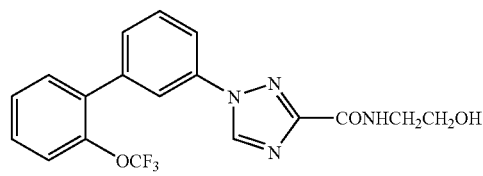

N-(2-Hydroxyeth-1-yl)-1-[3-((2-trifluoromethoxy)phenyl)-phenyl]-1,24-triazole-3-carboxamide Mass Spectrum (ESI) m/e M+1 393.1.

EXAMPLE 45

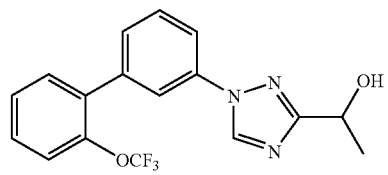

3-(1-Hydroxy)eth-1-yl-1-[3-((2-trifluoromethoxy)phenyl)-phenyl]-1,2,4-triazole

The title compound was prepared according to procedures described in Example 32.

Mass Spectrum (ESI) m/e M+1 350.1.

EXAMPLE 46

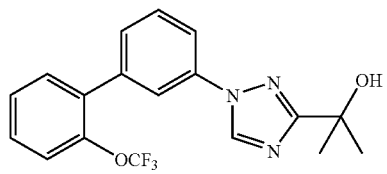

3-(1-Hydroxy-1-methyl)eth-1-yl-1-[3-((2-trifluoromethoxy)phenyl)-phenyl]-1,2,4-triazole The title compound was isolated according to the procedure for preparing the compound of Example 45.

Mass Spectrum (ESI) m/e M+1 364.0.

EXAMPLE 47

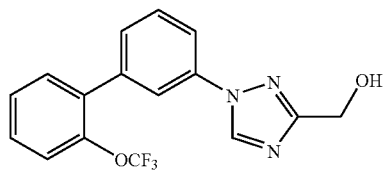

3-Hydroxymethyl-1-[3-((2-trifluoromethoxy)-phenyl)-phenyl]-1,2,4-triazole

The title compound was isolated according to the procedure for preparing the compound of Example 45.

Mass Spectrum (ESI) m/e M+1 336.1.

EXAMPLE 48

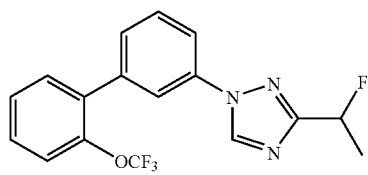

3-(1-Fluoro)-eth-1-yl-1-[3-((2-trifluoromethoxy)-phenyl)-phenyl]-1,2,4-triazole

The title compound was prepared from 3-(1-hydroxy)-eth-1-yl-1-[3-((2-trifluoromethoxy)phenyl)-phenyl]-1,2,4-triazole (Example 45) according to procedures described in Example 35.

Mass Spectrum (ESI) m/e M+1 352.0.

EXAMPLE 49

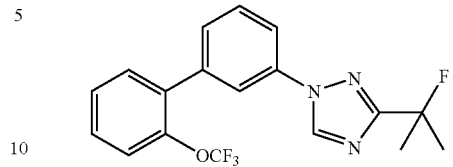

3-(1-Fluoro-1-methyl)-eth-1-yl-1-[3-((2-trifluoromethoxy)-phenyl)-phenyl]-1,2,4-triazole The title compound was prepared from 3-(1-hydroxy-1-methyl)eth-1-yl-1-[3-((2-trifluoromethoxy)phenyl)-phenyl]-1,2,4-triazole (Example 46) according to procedures described in Example 35.

Mass Spectrum (ESI) m/e M+1 366.1.

EXAMPLE 50

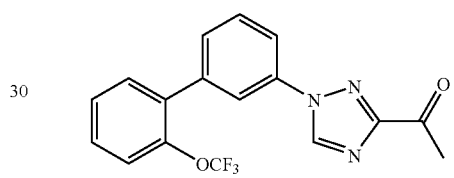

3-(1-Oxo)-eth-1-yl-1-[3-((2-trifluoromethoxy)-phenyl)-phenyl]-1,2,4-triazole

The title compound was prepared from 1-[3-((2-Trifluoroethoxy)-phenyl)-phenyl]-1,2,4-triazole-3-carboxylic acid (from Example 38) according to procedures described in Example 36.

Mass Spectrum (ESI) m/e M+1 348.1.

EXAMPLE 51

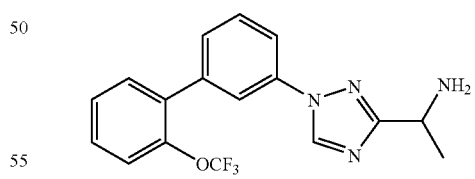

3-(1-Amino)-eth-1-yl-1-[3-((2-trifluoromethoxy)-phenyl)-phenyl]-1,2,4-triazole

A solution of 0.037 g (0.106 mmol) of 3-(1-oxo)-eth-1-yl-1-[3-((2-trifluoromethoxy)-phenyl)-phenyl]-1,2,4-triazole (Example 50), 0.082 g (1.06 mmol) of NH$_4$Oac and 0.1 Ml (0.72 mmol) of triethylamine in 1 Ml of THF was stirred for 2 hr. To the reaction mixture was added 0.045 g (0.212) of sodium triacetoxy-borohydride and 0.02 Ml (0.212 mmol) of acetic acid. The reaction mixture was stirred at RT for 72 hr. The reaction mixture was diluted with Saturated NaHCO₃ solution and the mixture was stirred for 45 min. The reaction mixture was extracted with diethyl ether and combined organic fractions were washed with brine, dried over Na₂SO₄, filtered and the filtrate was concentrated. The residue was purified by chromatography (silica, 1:1 EtOAc:hexanes, 1% methanol:CH₂Cl₂, 10% methanol:CH₂Cl₂ successively) to give the title compound.

Mass Spectrum (ESI) m/e M+1 349.1

EXAMPLE 52

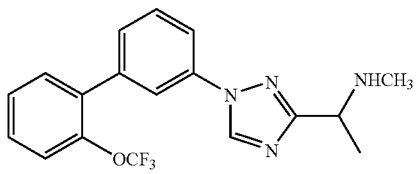

3-(1-N-methylamino)-eth-1-yl-1-[3-((2-trifluoromethoxy)-phenyl)-phenyl]-1,2,4-triazole The title compound was prepared according to procedures described in Example 51. Mass Spectrum (ESI) m/e M+1 363.1.

EXAMPLE 53

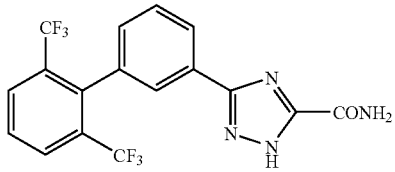

3-[3-((2,6-Bis-trifluoromethyl)-phenyl)-phenyl]-1,2,4-triazole-5-carboxamide

The titled compound is prepared using procedures described in Examples 19 and 20.

EXAMPLE 54

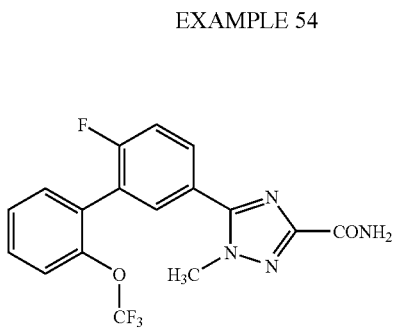

Mass Spectrum (ESI) m/e M+1 381.

What is claimed is:

1. A compound which is

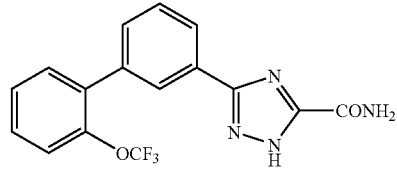

or a pharmaceutically acceptable salt thereof.

2. A compound which is

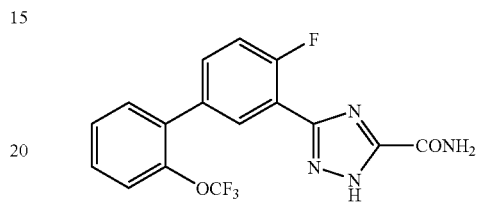

or a pharmaceutically acceptable salt thereof.

3. A compound which is

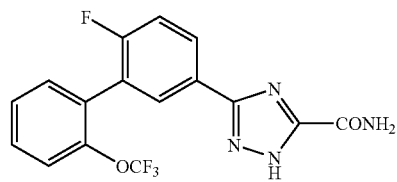

or a pharmaceutically acceptable salt thereof.

4. A compound which is

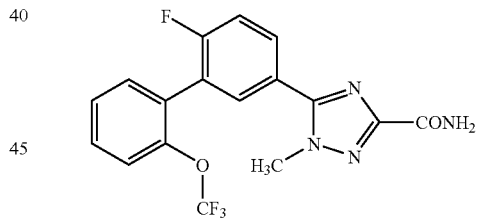

or a pharmaceutically acceptable salt thereof.

5. A compound which is

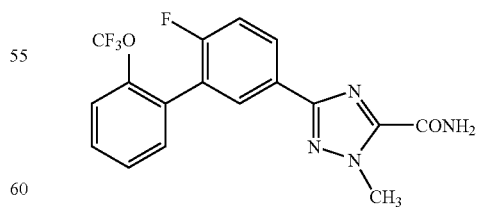

or a pharmaceutically acceptable salt thereof.

6. A pharmaceutical composition comprising a therapeutically effective amount of a compound according to claim 2, or a pharmaceutically acceptable salt thereof, and a pharmaceutically acceptable carrier.

7. A pharmaceutical composition comprising a therapeutically effective amount of a compound according to claim 3, or a pharmaceutically acceptable salt thereof, and a pharmaceutically acceptable carrier.

8. A pharmaceutical composition comprising a therapeutically effective amount of a compound according to claim 4, or a pharmaceutically acceptable salt thereof, and a pharmaceutically acceptable carrier.

9. A pharmaceutical composition comprising a therapeutically effective amount of a compound according to claim 5, or a pharmaceutically acceptable salt thereof, and a pharmaceutically acceptable carrier.

10. A method of treatment of neurogenic or infammatory pain comprising the step of administering to a patient in need thereof a therapeutically effective amount of a compound according to claim 2, or a pharmaceutically acceptable salt thereof.

11. A method of treatment of neurogenic or infammatory pain comprising the step of administering to a patient in need thereof a therapeutically effective amount of a compound according to claim 3, or a pharmaceutically acceptable salt thereof.

12. A method of treatment of neurogenic or infammatory pain comprising the step of administering to a patient in need thereof a therapeutically effective amount of a compound according to claim 4, or a pharmaceutically acceptable salt thereof.

13. A pharmaceutical composition comprising a therapeutically effective amount of a compound according to claim 5, or a pharmaceutically acceptable salt thereof.

* * * * *